(12) United States Patent
Wang et al.

(10) Patent No.: US 8,987,264 B2
(45) Date of Patent: Mar. 24, 2015

(54) 1,3,5-TRIAZINE DERIVATIVES OF SPIRO BICYCLIC OXALAMIDE-COMPOUNDS FOR TREATMENT OF HEPATITIS C

(71) Applicant: Bristol-Myers Squibb Company, Princeton, NJ (US)

(72) Inventors: Tao Wang, Farmington, CT (US); Zhiwei Yin, Glastonbury, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/073,963

(22) Filed: Nov. 7, 2013

(65) Prior Publication Data
US 2014/0135335 A1 May 15, 2014

Related U.S. Application Data

(60) Provisional application No. 61/724,388, filed on Nov. 9, 2012.

(51) Int. Cl.
| | |
|---|---|
| A61K 31/53 | (2006.01) |
| C07D 251/52 | (2006.01) |
| C07D 487/10 | (2006.01) |
| A61K 45/06 | (2006.01) |

(52) U.S. Cl.
CPC .............. C07D 487/10 (2013.01); A61K 31/53 (2013.01); A61K 45/06 (2013.01)
USPC ........... 514/245; 544/219; 246/146; 246/245; 248/128; 248/202; 248/214; 248/453

(58) Field of Classification Search
CPC ................................ A61K 31/53; C07D 251/52
USPC .................. 514/245; 544/219; 546/146, 245; 548/128, 202, 214, 453
See application file for complete search history.

(56) References Cited

U.S. PATENT DOCUMENTS

2009/0286778 A1   11/2009   Combs et al.

FOREIGN PATENT DOCUMENTS

WO   WO 2009/091388   7/2009

OTHER PUBLICATIONS

Alter, et al., "The Prevalence of Hepatitis C Virus Infection in the United States, 1988 through 1994," The New England Journal of Medicine, vol. 341, No. 8, pp. 556-562 (Aug. 19, 1999).
Barth, et al., "Cellular Binding of Hepatitis C Virus Envelope Glycoprotein E2 Requires Cell Surface Heparan Sulfate," Journal of Biological Chemistry, vol. 278, No. 42, pp. 41003-41012 (Oct. 17, 2003).
Bartosch, et al., "Infectious Hepatitis C Virus Pseudo-particles Containing Functional E1-E2 Envelope Protein Complexes," Journal of Experimental Medicine, vol. 197, No. 5, pp. 633-642 (Mar. 3, 2003).
Boyer, et al., "Pathogenesis, diagnosis and management of hepatitis C," Journal of Hepatology, 32 (Suppl. 1), pp. 98-112 (2000).
Fried, et al., "Peginterferon Alfa-2a Plus Ribavirin for Chronic Hepatitis C Virus Infection," New England Journal of Medicine, vol. 347, No. 13, pp. 975-982 (Sep. 26, 2002).
Hsu, et al., "Hepatitis C virus glycoproteins mediate pH-dependent cell entry of pseudotyped retroviral particles," Proc. Natl. Acad. Sci. USA, vol. 100, No. 12, pp. 7271-7276 (Jun. 10, 2003).
Lindenbach, et al., "Complete Replication of Hepatitis C Virus in Cell Culture," Science, vol. 309, pp. 623-626 (Jul. 22, 2005).
Lindenbach, et al., "Unravelling hepatitis C virus replication from genome to function," Nature, vol. 436, pp. 933-938 (Aug. 18, 2005).
Lohmann, et al., "Replication of Subgenomic Hepatitis C Virus RNAs in a Hepatoma Cell Line," Science, Jul. 2, 1999, vol. 285, pp. 110-113.
Moradpour, et al., "Replication of hepatitis C virus," Nature Reviews Microbiology, vol. 5, pp. 453-463 (Jun. 2007).
Simmonds, "Genetic diversity and evolution of hepatitis C virus—15 years on," Journal of General Virology, vol. 85, pp. 3173-3188 (2004).
Wakita, et al., "Production of infectious hepatitis C virus in tissue culture from a cloned viral genome," Nature Medicine, vol. 11, No. 7, pp. 791-796 (Jul. 2005).
Zeuzem, "Interferon-based therapy for chronic hepatitis C: current and future perspectives," Nature Clinical Practice Gastroenterology & Hepatology, vol. 5, No. 11, pp. 610-622 (Nov. 2008).
Remington: Pharmaceutical Sciences, 17th edition, pp. xv-xvi, Mack Publishing Company, Easton, PA, publ. (1985) (table of contents).

*Primary Examiner* — Douglas M Willis

(74) *Attorney, Agent, or Firm* — John F. Levis

(57) ABSTRACT

Compounds of Formula I, including pharmaceutically acceptable salts, as well as compositions containing these compounds, have activity against hepatitis C virus (HCV) and may be useful in treating those infected with HCV:

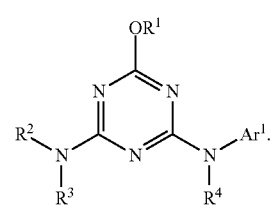

14 Claims, No Drawings

1,3,5-TRIAZINE DERIVATIVES OF SPIRO BICYCLIC OXALAMIDE-COMPOUNDS FOR TREATMENT OF HEPATITIS C

CROSS REFERENCE TO RELATED APPLICATION

This non-provisional application claims the benefit of U.S. Provisional Application Ser. No. 61/724,388 filed Nov. 9, 2012.

FIELD OF THE INVENTION

The invention relates to the novel compounds of formula I, including pharmaceutically acceptable salts thereof, which have activity against hepatitis C virus (HCV) and are useful in treating those infected with HCV. The invention also relates to compositions and methods of using these compounds, as well as to methods for making these compounds.

BACKGROUND OF THE INVENTION

Hepatitis C virus (HCV) chronically infects an estimated 170 million people worldwide, with 3 to 4 million infected individuals in the United States alone (Boyer, N. and Marcellin, P. *J. Hepatology.*, 2000, 32:98-112; Alter, M. J., et al. *Engl. J. Med.* 1999,1999, 341:556-562). Prior to the mid 1990s, transfusion with infected blood products was the main route of HCV transmission. Following the introduction of blood screening methods, transmission via injection drug use became the primary risk factor. Chronic infection often leads to the development of severe liver complications, including fibrosis, cirrhosis, and hepatocellular carcinoma. HCV infection is also the leading cause of orthotopic liver transplantation in the United States. The degree to which disease progression is related to viral and cellular factors is not completely understood.

Considerable heterogeneity is found within the nucleotide and encoded amino acid sequence of the HCV genome (Simmonds, P. *J. Gen. Virology.*, 2004, 85:3173-3188). Based on this sequence diversity, six major genotypes and multiple associated subtypes have been described. The genotypes of HCV differ in their worldwide distribution, and the clinical significance of the genetic heterogeneity of HCV remains elusive despite numerous studies of the possible effect of genotypes on pathogenesis and therapy.

Medical treatment for HCV is limited by the lack of a vaccine or approved therapies that specifically target the virus. Currently, patients undergo treatment with a combination of parenterally administered pegylated alpha-interferon and oral ribavirin. Genotype 1 HCV is the most difficult to treat and elimination of the virus (sustained virologic response) is achieved for only approximately 50% of patients (Fried, M. W. et al. *N. Engl. J. Med.*, 2002, 347:975-982; Zeumzem, S. *Nature Clinical Practice.*, 2008, 5:610-622). This poor treatment response, combined with often severe side effects induced by therapy, highlight a need for improved antiviral drugs with better efficacy and safety profiles.

HCV is a member of the Flaviviridae family of viruses with a single-stranded positive-sense RNA genome. Following infection of host cells, the 9.6 Kb genome is translated into a polyprotein precursor of approximately 3,000 amino acids (reviewed in Lindenbach, B. D. and Rice, C. M. *Nature.*, 2005, 436:933-938; Moradpour, D, Penin, F., and Rice, C. M. *Nature Reviews.*, 2007, 5:453-463). Post-translational processing by both cellular and viral proteases results in the generation of at least 10 separate viral proteins. The structural proteins (which by definition are found in mature virions) include core, E1, E2, and possibly p7, and originate from the amino-terminal region of the polyprotein. The core protein assembles into the viral nucleocapsid. The E1 and E2 glycoproteins form heterodimers that are found within the lipid envelope surrounding the viral particles, and mediate host cell receptor binding and entry of the virus into cells. It is unclear if p7 is a structural protein, and its role in replication has yet to be defined. However p7 is believed to form an ion channel in cellular membranes, preventing acidification of intracellular compartments in which virions are assembled, and it has been shown to be essential for viral replication and assembly. The nonstructural proteins NS2, NS3, NS4A, NS4B, NS5A, and NS5B are produced through maturational cleavages of the carboxy-terminal region of the polyprotein. NS2 along with the amino terminus of NS3 form the NS2-3 metalloprotease which cleaves at the NS2-NS3 junction. Additionally, NS2 is involved in assembly and egress of nascent virions. The NS3 protein contains both a serine protease in its amino-terminal region, and a nucleotide-dependent RNA helicase in its carboxy-terminal region. NS3 forms a heterodimer with the NS4A protein, constituting the active protease which mediates cleavages of the polyprotein downstream of NS3, both in cis, at the NS3-NS4A cleavage site, and in trans, for the remaining NS4A-NS4B, NS4B-NS5A, NS5A-NS5B sites. The complex formation of the NS3 protein with NS4A seems necessary to the processing events, enhancing the proteolytic efficiency at all of the sites. The NS3 protein also exhibits nucleoside triphosphatase and RNA helicase activities. The NS4B protein has been shown to be important for localization of HCV proteins into replication complexes in altered membranous structures within the cell. NS5B encodes an RNA-dependent RNA polymerase that is involved in the replication of HCV.

Subgenomic HCV replicons, containing the untranslated regions 5' and 3' to the coding sequence fused to the nonstructural proteins or the full-length polyprotein, are competent for translation, viral protein expression, and replication within cultured cells (Lohmann, V. et al. *Science.*, 1999, 285:110-113; Moradpour, D, Penin, F., and Rice, C. M. *Nature Reviews.*, 2007, 5:453-463). The replicon system has proven valuable for the identification of inhibitors targeting the nonstructural proteins associated with these functions. However, only limited subsets of HCV genotypes have been used to generate functional replicons.

Other systems have been used to study the biology of the HCV structural proteins that mediate the entry into host cells. For example, virus-like-particles made in recombinant baculovirus-infected cells with the HCV core, E1 and E2 proteins have also been used to study the function of the HCV E1 and E2 proteins (Barth, H., et al. *J. Biol. Chem.*, 2003, 278:41003-41012). In addition, pseudotyping systems where the E1 and E2 glycoproteins are used to functionally replace the glycoproteins of retroviruses have been developed (Bartosch, B., Dubuisson, J. and Cosset, F.-L. *J. Exp. Med.*, 2003, 197:633-642; Hsu, M. et al. *Proc. Natl. Acad. Sci. USA.*, 2003, 100: 7271-7276). These systems yield HCV pseudoparticles that bind to and enter host cells in a manner which is believed to be analogous to the natural virus, thus making them a convenient tool to study the viral entry steps as well as to identify inhibitors block this process.

Recently, a full-length genotype 2a HCV clone, JFH1, was isolated and demonstrated the ability to replicate in vitro. Through repeated passage and adaptation in cell culture increased titers of infectious virus were produced (Lindenbach, B. D., et al. *Science.*, 2005, 309:623-626; Wakita, T. et al. *Nature Med.*, 2005, 11:791-796). In contrast to the HCV replicon or pseudotyping systems, the infectious virus is useful for studying the complete HCV replication cycle, including identifying inhibitors of not only the replication proteins, but those involved in early steps in virus infection (entry and uncoating) and production of progeny viruses (genome packaging, nucleocapsid assembly, virion envelopment and egress).

Triazines have been disclosed, in particular in WO 2009/091388 and US 2009/0286778.

What is now needed in the art are more compounds which are novel and effective against hepatitis C. Additionally, these compounds should provide advantages for pharmaceutical uses, for example, with regard to one or more of their mechanisms of action, binding, inhibition efficacy, target selectivity, solubility, safety profiles, or bioavailability. Also needed are new compositions and methods of treating HCV infection.

SUMMARY OF THE INVENTION

One aspect of the invention is one or more compounds of Formula I, including pharmaceutically acceptable salts thereof:

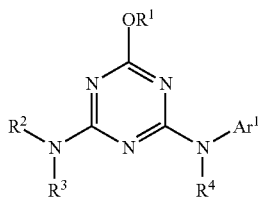

wherein
$R^1$ is selected from alkyl, hydroxyalkyl, alkoxyalkyl, haloalkyl, cycloalkyl, hydroxycycloalkyl, alkoxycycloalkyl, halocycloalkyl, cycloalkenyl, indanyl, alkylcarbonyl, and benzyl, wherein the benzyl moiety is substituted with 0-3 substituents selected from halo, alkyl, haloalkyl, alkoxy, and haloalkoxy;
$R^2$ is selected from alkyl, $(Ar^2)$alkyl, $(Ar^2)$cycloalkyl, $((Ar^2)$cycloalkyl)alkyl, $((Ar^2)$alkyl)cycloalkyl, and $(((Ar^2)$alkyl)cycloalkyl)alkyl;
$R^3$ is hydrogen or alkyl;
$R^4$ is hydrogen or alkyl;
$R^5$ is selected from

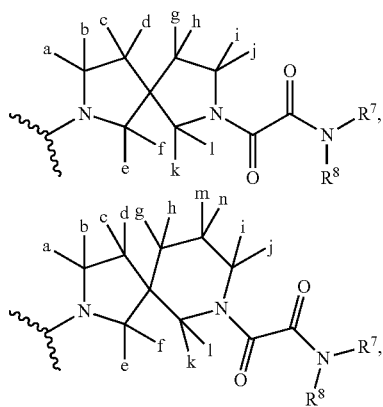

$R^6$ is selected from halo, alkyl, haloalkyl, alkoxy, and haloalkoxy;
$R^7$ is selected from alkyl, cycloalkyl, (cycloalkyl)alkyl, (alkyl)cycloalkyl, ((alkyl))cycloalkyl)alkyl, and a bridged bicycloalkyl, and is substituted with 0-4 substituents selected from halo, alkyl, cycloalkyl, hydroxyalkyl, alkoxyalkyl, hydroxy, alkoxy, benzyloxy, $CO_2R^9$, $N(R^{10})(R^{11})$, tetrahydrofuranyl, tetrahydropyranyl, and $Ar^4$;
or $R^7$ is hydrogen, N-alkoxycarbonylpiperidinyl, piperidinonyl, or $Ar^3$;

$R^8$ is hydrogen or alkyl;

or $R^7$ and $R^8$ taken together with the nitrogen to which they are attached is selected from azetidinyl, pyrrolidinyl, piperidinyl, piperazinyl, and morpholinyl, and is substituted with 0-2 substituents selected from alkyl, alkylcarbonyl, and alkoxycarbonyl;

$R^9$ is selected from hydrogen, alkyl, hydroxyalkyl, alkoxyalkyl, ((hydroxyalkyl)alkoxy)alkoxy, and ((alkoxy)alkoxy)alkoxy;

$R^{10}$ is selected from hydrogen, alkyl, cycloalkyl, alkylcarbonyl, and alkoxycarbonyl;

$R^{11}$ is hydrogen or alkyl;

or $R^{10}$ and $R^{11}$ taken together with the nitrogen to which they are attached is selected from azetidinyl, pyrrolidinyl, piperidinyl, piperazinyl, and morpholinyl, and is substituted with 0-2 substituents selected from alkyl, alkylcarbonyl, and alkoxycarbonyl;

$R^{12}$ is hydrogen or alkyl;

$R^{13}$ is selected from hydrogen, alkyl, cycloalkyl, alkylcarbonyl, and alkoxycarbonyl;

$R^{14}$ is hydrogen or alkyl;

or $R^{13}$ and $R^{14}$ taken together with the nitrogen to which they are attached is selected from azetidinyl, pyrrolidinyl, piperidinyl, piperazinyl, and morpholinyl, and is substituted with 0-2 substituents selected from alkyl, alkylcarbonyl, and alkoxycarbonyl;

$Ar^1$ is phenyl substituted with 1 $CO(R^5)$ and with 0-3 substituents selected from $R^6$;

$Ar^2$ is phenyl substituted with 0-3 substituents selected from halo, alkyl, haloalkyl, alkoxy, and haloalkoxy;

$Ar^3$ is selected from phenyl, indanyl, fluorenyl, biphenyl, terphenyl, pyridinyl, pyrazolyl, isoxazolyl, imidazolyl, thiazolyl, thiadiazolyl, triazolyl, benzoxazolyl, indolinyl, and dibenzofuranyl, and is substituted with 0-3 substituents selected from cyano, halo, alkyl, alkenyl, haloalkyl, cycloalkyl, $(CO_2R^{12})$alkyl, $(CO_2R^{12})$alkenyl, $(CON(R^{13})(R^{14}))$alkyl, phenyl, hydroxyl, alkoxy, haloalkoxy, alkylcarbonyl, $CO_2R^{12}$, $CON(R^{13})(R^{14})$, and $PhCONHSO_2$;

or $Ar^3$ is phenyl substituted with 1 substituent selected from benzyl, tetrazolyloxy, thiazolyl, phenylpyrazolyl, methyloxadiazolyl, thiadiazolyl, triazolyl, methyltriazolyl, tetrazolyl, pyridinyl, and dimethoxypyrimdinyl;

$Ar^4$ is selected from phenyl, indanyl, tetrahydronaphthyl, isochromanyl, benzodioxolyl, pyridinyl, pyrazolyl, imidazolyl, and triazolyl, and is substituted with 0-3 substituents selected from cyano, halo, alkyl, alkyenyl, haloalkyl, alkoxy, haloalkoxy, $N(R^{13})(R^{14})$, and alkylCO; and wherein a, b, c, d, e, f, g, h, i, j, k, l, m, n, o, p are each independently hydrogen, alkyl, or cycloalkyl.

In a further embodiment, there is provided a method for treating a patient infected with a virus, especially wherein said virus is HCV, comprising administering to said patient an antiviral effective amount of one or more compounds of Formula I above, and one or more pharmaceutically acceptable carriers, excipients or diluents. Optionally, the compound(s) of Formula I can be administered in combination with an antiviral effective amount of another-HCV treatment agent.

Another embodiment of the present invention is a pharmaceutical composition comprising an antiviral effective amount of one or more compounds of Formula I, and one or more pharmaceutically acceptable carriers, excipients, and diluents; and optionally in combination with an antiviral effective amount of another HCV treatment agent.

In another embodiment of the invention there is provided one or more methods for making the compounds of Formula I herein.

Also provided herein are intermediate compounds useful in making the compounds of Formula I herein.

The present invention is directed to these, as well as other important ends, hereinafter described.

DETAILED DESCRIPTION OF THE EMBODIMENTS

Unless otherwise specifically set forth elsewhere in the application, these terms shall have the following meanings. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 8 carbons. "Alkylene" means a straight or branched divalent alkyl group. "Alkenylene" means a straight or branched divalent alkyl group with at least one double bond. "Cycloalkylene" means a divalent cycloalkane moiety composed of 3 to 7 carbons and includes gem-divalency (for example 1,1-cyclopropanediyl) as well as non-gem-divalency (for example, 1,4-cyclohexanediyl). "Alkylidinyl" means a divalent alkene substituent where the divalency occurs on the same carbon of the alkene. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Phenylene is a divalent benzene ring. "1,4-Phenylene" means 1,4-benzenediyl with respect to regiochemistry for the divalent moiety. Parenthetic and multiparenthetic terms are intended to clarify bonding relationships to those skilled in the art. For example, a term such as ((R)alkyl) means an alkyl substituent further substituted with the substituent R.

The substituents described above may be attached at any suitable point of attachment unless otherwise specified. However, it is understood that the compounds encompassed by the present invention are those that are chemically stable as understood by those skilled in the art. Additionally, the compounds encompassed by the present disclosure are those that are suitably stable for use as a pharmaceutical agent.

As set forth, the invention includes all pharmaceutically acceptable salt forms of the compounds of Formula I. Pharmaceutically acceptable salts are those in which the counter ions do not contribute significantly to the physiological activity or toxicity of the compounds, and as such function as pharmacological equivalents. These salts can be made according to accepted organic techniques employing commercially available reagents. By way of non-limiting example, some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

As set forth above, the invention is directed to one or more compounds of Formula I, including pharmaceutically acceptable salts thereof:

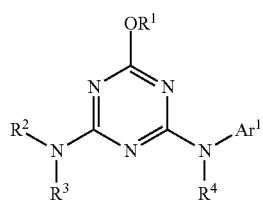

I wherein
$R^1$ is selected from alkyl, hydroxyalkyl, alkoxyalkyl, haloalkyl, cycloalkyl, hydroxycycloalkyl, alkoxycycloalkyl, halocycloalkyl, cycloalkenyl, indanyl, alkylcarbonyl, and benzyl, wherein the benzyl moiety is substituted with 0-3 substituents selected from halo, alkyl, haloalkyl, alkoxy, and haloalkoxy;
$R^2$ is selected from alkyl, $(Ar^2)$alkyl, $(Ar^2)$cycloalkyl, $((Ar^2)$cycloalkyl)alkyl, $((Ar^2)$alkyl)cycloalkyl, and $(((Ar^2)$alkyl)cycloalkyl)alkyl;
$R^3$ is hydrogen or alkyl;
$R^4$ is hydrogen or alkyl;
$R^5$ is selected from

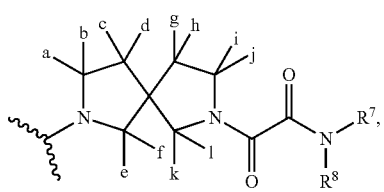

$R^6$ is selected from halo, alkyl, haloalkyl, alkoxy, and haloalkoxy;

R⁷ is selected from alkyl, cycloalkyl, (cycloalkyl)alkyl, (alkyl)cycloalkyl, ((alkyl))cycloalkyl)alkyl, and a bridged bicycloalkyl, and is substituted with 0-4 substituents selected from halo, alkyl, cycloalkyl, hydroxyalkyl, alkoxyalkyl, hydroxy, alkoxy, benzyloxy, CO₂R⁹, N(R¹⁰)(R¹¹), tetrahydrofuranyl, tetrahydropyranyl, and Ar⁴;

or R⁷ is hydrogen, N-alkoxycarbonylpiperidinyl, piperidinonyl, or Ar³;

R⁸ is hydrogen or alkyl;

or R⁷ and R⁸ taken together with the nitrogen to which they are attached is selected from azetidinyl, pyrrolidinyl, piperidinyl, piperazinyl, and morpholinyl, and is substituted with 0-2 substituents selected from alkyl, alkylcarbonyl, and alkoxycarbonyl;

R⁹ is selected from hydrogen, alkyl, hydroxyalkyl, alkoxyalkyl, ((hydroxyalkyl)alkoxy)alkoxy, and ((alkoxy)alkoxy)alkoxy;

R¹⁰ is selected from hydrogen, alkyl, cycloalkyl, alkylcarbonyl, and alkoxycarbonyl;

R¹¹ is hydrogen or alkyl;

or R¹⁰ and R¹¹ taken together with the nitrogen to which they are attached is selected from azetidinyl, pyrrolidinyl, piperidinyl, piperazinyl, and morpholinyl, and is substituted with 0-2 substituents selected from alkyl, alkylcarbonyl, and alkoxycarbonyl;

R¹² is hydrogen or alkyl;

R¹³ is selected from hydrogen, alkyl, cycloalkyl, alkylcarbonyl, and alkoxycarbonyl;

R¹⁴ is hydrogen or alkyl;

or R¹³ and R¹⁴ taken together with the nitrogen to which they are attached is selected from azetidinyl, pyrrolidinyl, piperidinyl, piperazinyl, and morpholinyl, and is substituted with 0-2 substituents selected from alkyl, alkylcarbonyl, and alkoxycarbonyl;

Ar¹ is phenyl substituted with 1 CO(R⁵) and with 0-3 substituents selected from R⁶;

Ar² is phenyl substituted with 0-3 substituents selected from halo, alkyl, haloalkyl, alkoxy, and haloalkoxy;

Ar³ is selected from phenyl, indanyl, fluorenyl, biphenyl, terphenyl, pyridinyl, pyrazolyl, isoxazolyl, imidazolyl, thiazolyl, thiadiazolyl, triazolyl, benzoxazolyl, indolinyl, and dibenzofuranyl, and is substituted with 0-3 substituents selected from cyano, halo, alkyl, alkenyl, haloalkyl, cycloalkyl, (CO₂R¹²)alkyl, (CO₂R¹²)alkenyl, (CON(R¹³)(R¹⁴))alkyl, phenyl, hydroxyl, alkoxy, haloalkoxy, alkylcarbonyl, CO₂R¹², CON(R¹³)(R¹⁴), and PhCONHSO₂;

or Ar³ is phenyl substituted with 1 substituent selected from benzyl, tetrazolyloxy, thiazolyl, phenylpyrazolyl, methyloxadiazolyl, thiadiazolyl, triazolyl, methyltriazolyl, tetrazolyl, pyridinyl, and dimethoxypyrimdinyl;

Ar⁴ is selected from phenyl, indanyl, tetrahydronaphthyl, isochromanyl, benzodioxolyl, pyridinyl, pyrazolyl, imidazolyl, and triazolyl, and is substituted with 0-3 substituents selected from cyano, halo, alkyl, alkyenyl, haloalkyl, alkoxy, haloalkoxy, N(R¹³)(R¹⁴), and alkylCO; and wherein a, b, c, d, e, f, g, h, i, j, k, l, m, n, o, p are each independently hydrogen, alkyl, or cycloalkyl.

Any scope of any variable, including R¹, R², R³, R⁴, R⁵, R⁶, R⁷, R⁸, R⁹, R¹⁰, R¹¹, R¹², R¹³, R¹⁴, L, Ar¹, Ar², Ar³, Ar⁴, a, b, c, d, e, f, g, h, i, j, k, l, m, n, o, p can be used independently with the scope of any other instance of a variable.

In a further embodiment, R¹ is haloalkyl. Preferably, R¹ can be trifluoroethyl.

In another embodiment, R² is (Ar²)alkyl or (Ar²)cycloalkyl.

In another embodiment, R³ is hydrogen and R⁴ is hydrogen.

In another embodiment, R⁷ is Ar³.

In another embodiment, Ar¹ is phenyl para-substituted with 1 CO(R⁵).

In another embodiment, R⁵ is

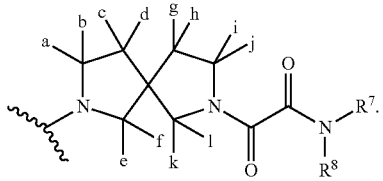

In a further embodiment, R¹ is haloalkyl; R² is (Ar²)alkyl or (Ar²)cycloalkyl; R³ is hydrogen; R⁴ is hydrogen; R⁷ is alkyl, cycloalkyl, (cycloalkyl)alkyl, (alkyl)cycloalkyl, ((alkyl))cycloalkyl)alkyl, or a bridged bicycloalkyl, and is substituted with 0-4 substituents selected from halo, alkyl, cycloalkyl, hydroxyalkyl, alkoxyalkyl, hydroxy, alkoxy, benzyloxy, CO₂R⁹, N(R¹⁰)(R¹¹), tetrahydrofuranyl, tetrahydropyranyl, and Ar⁴; R⁷ is Ar³; and Ar¹ is phenyl para-substituted with 1 CO(R⁵).

In another embodiment, R⁷ is alkyl, cycloalkyl, (cycloalkyl)alkyl, (alkyl)cycloalkyl, ((alkyl))cycloalkyl)alkyl, or a bridged bicycloalkyl, and is substituted with 0-4 substituents selected from halo, alkyl, cycloalkyl, hydroxyalkyl, alkoxyalkyl, hydroxy, alkoxy, benzyloxy, CO₂R⁹, N(R¹⁰)(R¹¹), tetrahydrofuranyl, tetrahydropyranyl, and Ar⁴.

Preferred compounds include those which are selected from

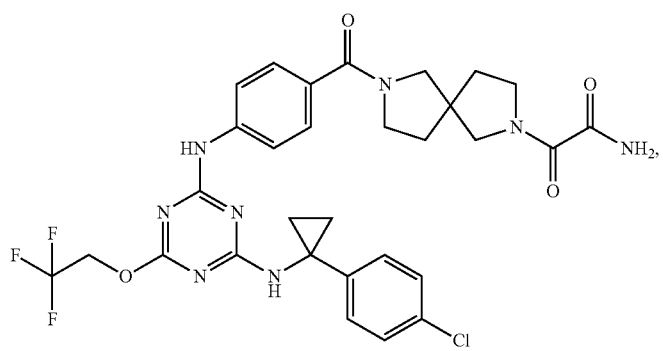

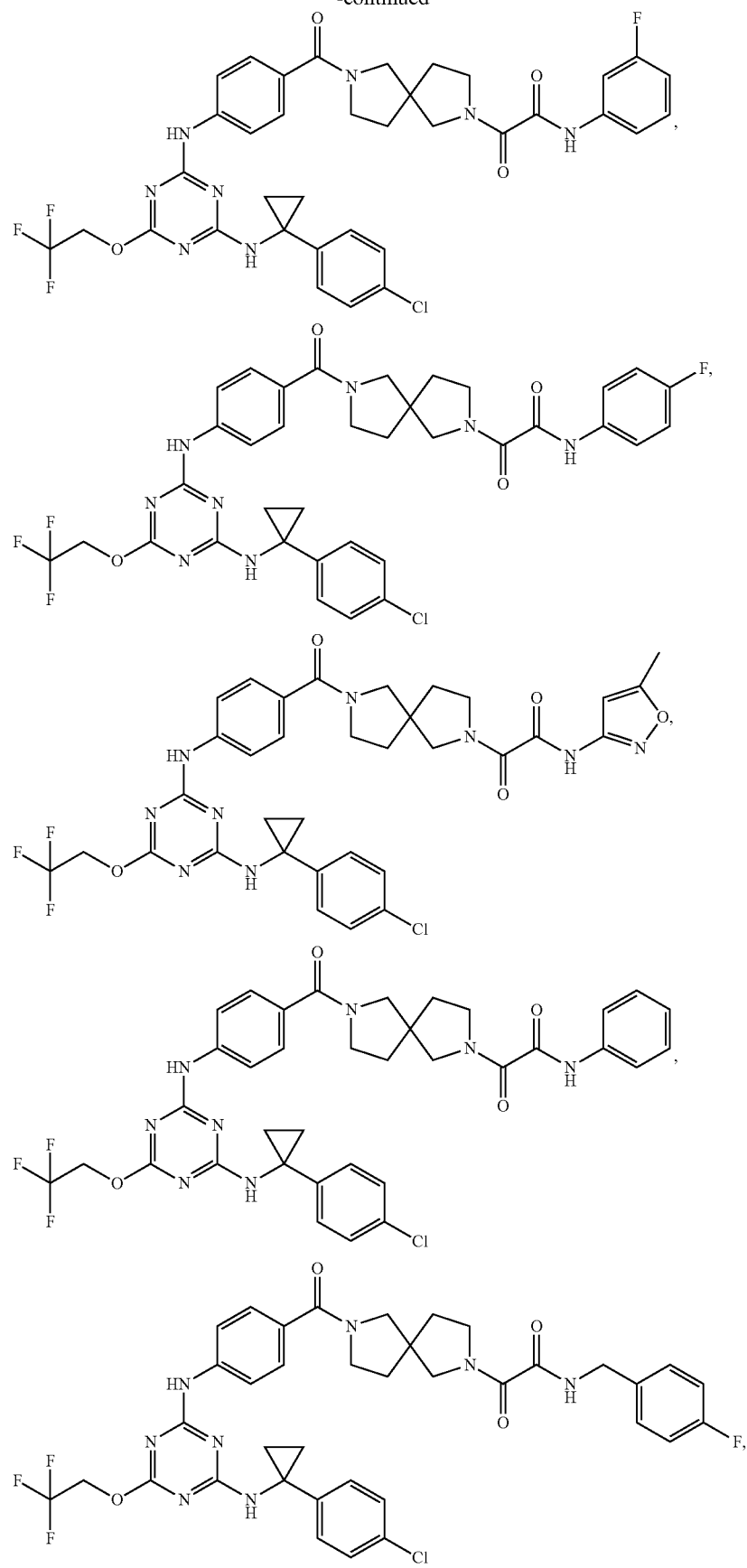

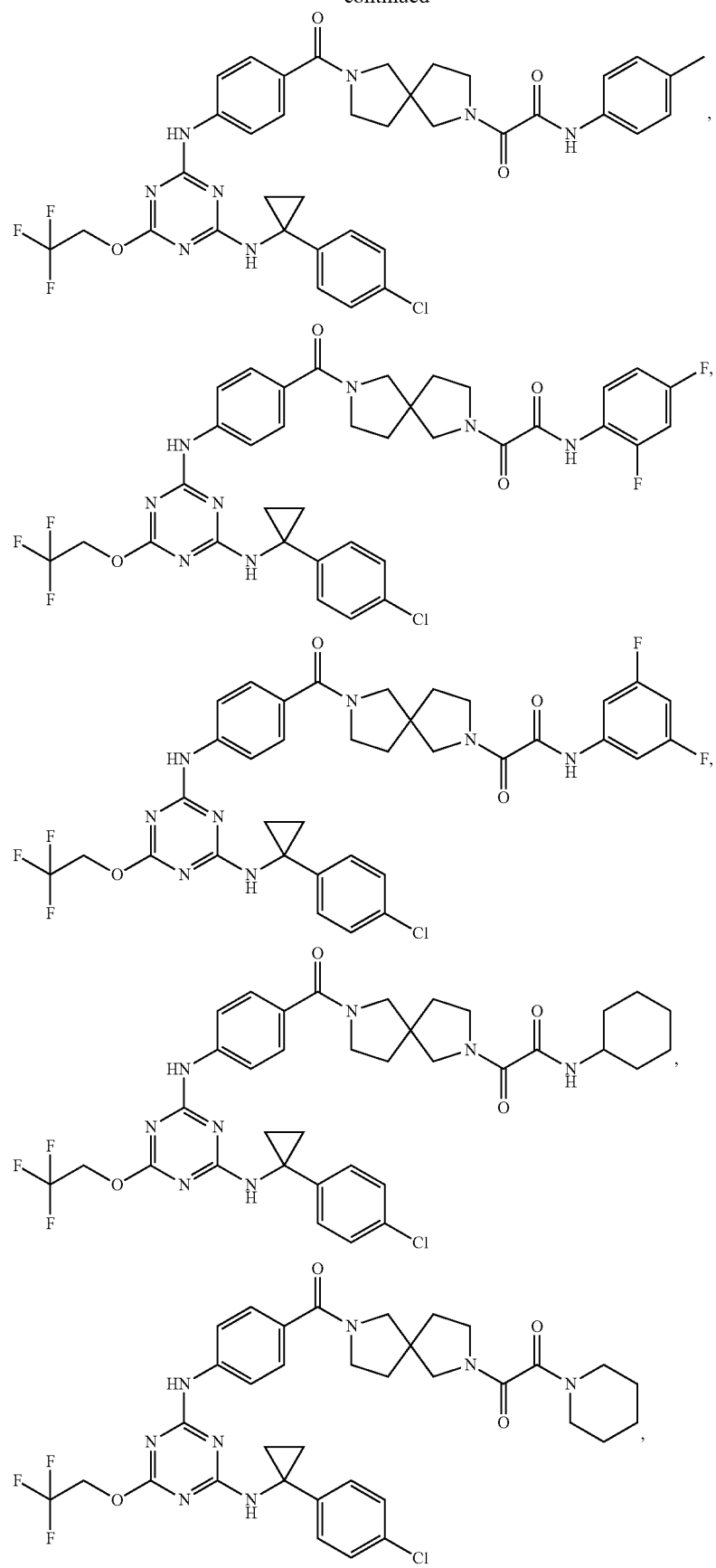

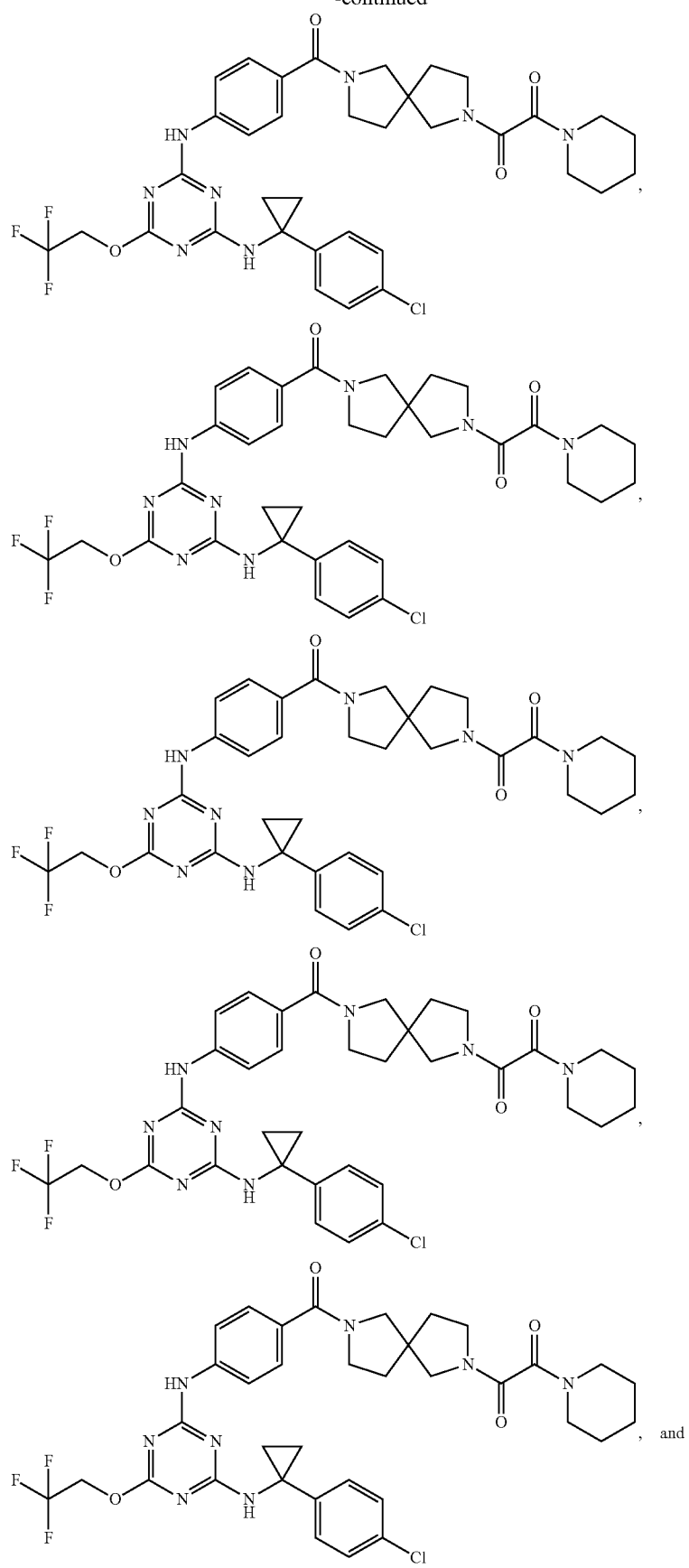

-continued

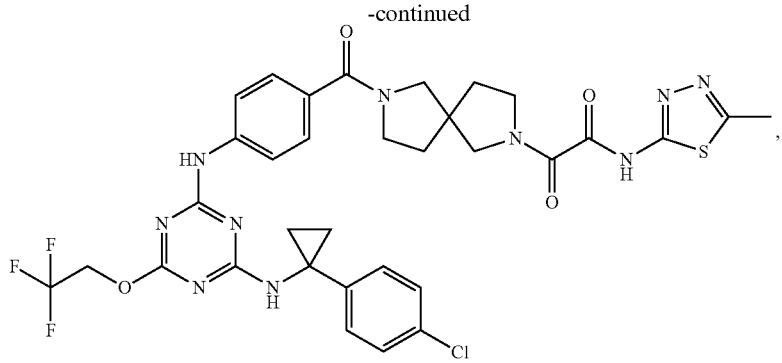

including pharmaceutically acceptable salts thereof.

Pharmaceutical Compositions and Methods of Treatment

The compounds of Formula I demonstrate activity against HCV NS5B and can be useful in treating HCV and HCV infection. Therefore, another aspect of the invention is a composition comprising one or more compounds of Formula I, and a pharmaceutically acceptable carrier.

Another aspect of the invention is a composition comprising one or more compounds of Formula I, and further comprising another compound having anti-HCV activity, and a pharmaceutically acceptable carrier.

In one embodiment of the composition, the other compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition wherein the other compound having anti-HCV activity is a cyclosporin. Another aspect of the invention is where the cyclosporin is cyclosporin A.

Another aspect of the invention is a composition wherein the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

Another aspect of the invention is a composition wherein the other compound having anti-HCV activity is effective in inhibiting the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is therefore a composition comprising one or more compounds of Formula I, a pharmaceutically acceptable carrier, an interferon, and ribavirin.

Another aspect of the invention is a method of inhibiting the function of the HCV replicon comprising contacting the HCV replicon with one or more compounds of Formula I.

Another aspect of the invention is a method of inhibiting the function of the HCV NS5B protein comprising contacting the HCV NS5B protein with one or more compounds of Formula I.

Another aspect of the invention is a method of treating an HCV infection in a patient comprising administering to the patient a therapeutically effective amount of one or more compounds of Formula I. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of one or more compounds of Formula I, in conjunction with (prior to, after, or concurrently) another compound having anti-HCV activity.

Another aspect of the invention is the method wherein the other compound having anti-HCV activity is an interferon or a ribavirin.

Another aspect of the invention is the method wherein the interferon is selected from interferon alpha 2B, pegylated interferon alpha, consensus interferon, interferon alpha 2A, interferon lambda, and lymphoblastoid interferon tau.

Another aspect of the invention is the method wherein the other compound having anti-HCV activity is a cyclosporin.

Another aspect of the invention is the method wherein the cyclosporin is cyclosporin A.

Another aspect of the invention is the method wherein the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

Another aspect of the invention is the method wherein the other compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method wherein the other compound having anti-HCV activity is effective to inhibit the function of target in the HCV life cycle other than the HCV NS5B protein.

"Therapeutically effective" or "anti-virally effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including, for example, capsules, tablets, lozenges, and powders, as well as liquid suspensions, syrups, elixers, and solutions. Compositions are made using available formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions which are normally formulated in dosage units and compositions providing from about 1 to 1000 mg of the active ingredient per dose are preferred. Some non-limiting examples of dosages are 1 mg, 10 mg, 100 mg, 250 mg, 500 mg, and 1000 mg. Generally, other agents may be present in a unit range similar to agents of that class used clinically. Typically, this is about 0.25-1000 mg/unit.

Liquid compositions are usually in dosage unit ranges. Generally, the liquid composition will be in a unit dosage range of about 1-100 mg/mL. Some non-limiting examples of dosages are 1 mg/mL, 10 mg/mL, 25 mg/mL, 50 mg/mL, and 100 mg/mL. Generally, other agents may be present in a unit range similar to agents of that class used clinically. Typically, this is about 1-100 mg/mL.

The invention encompasses all conventional modes of administration; oral and parenteral methods are often preferred. Generally, the dosing regimen will be similar to other agents used clinically. Typically, the daily dose will be about 1-100 mg/kg body weight daily. Generally, more compound is required orally and less parenterally. The specific dosing regimen, however, will be determined by a physician using sound medical judgment.

The invention also encompasses methods wherein the compound of Formula I is given in combination therapy. That is, the compound can be used in conjunction with, but separately from, other agents useful in treating hepatitis and HCV infection. In these combination methods, the compound will generally be given in a daily dose of about 1-100 mg/kg body weight daily in conjunction with one or more other agents. The other agents generally will be given in the amounts used therapeutically. The specific dosing regimen, however, will be determined by a physician using sound medical judgment.

Some non-limiting examples of other compounds suitable for compositions and methods herein are listed in Table 1.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/ Novartis |
| GL-60667 | Antiviral | NS5B Replicase Inhibitor | Gene Labs/ Novartis |

TABLE 1-continued

| Brand Name | Physiological Class | Type of Inhibitor or Target | Source Company |
|---|---|---|---|
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon - α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |

TABLE 1-continued

| Brand Name | Physiological Class | Type of Inhibitor or Target | Source Company |
|---|---|---|---|
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/ Bristol-Myers Squibb |

Methods of Synthesis

The compounds of Formula I may be made by methods available in the art, as well as those described below and including variations within the skill of the art. Some reagents and intermediates are available in the art. Other reagents and intermediates can be made by methods available in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC"; "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

LC/MS Method (i.e., compound Identification.

All Liquid Chromatography (LC) data were recorded on a Shimadzu LC-10AS or LC-20AS liquid chromotograph using a SPD-10AV or SPD-20A UV-Vis detector and Mass Spectrometry (MS) data were determined with a Micromass Platform for LC in electrospray mode.

HPLC Method (i.e., Compound Isolation).

Compounds purified by preparative HPLC were diluted in methanol (1.2 mL) and purified using a Shimadzu LC-8A or LC-10A or Dionex APS-3000 or Waters Acquity™ automated preparative HPLC system.

SYNTHESES OF INTERMEDIATES

Preparation of 4-(4-(1-(4-chlorophenyl)cyclopropylamino)-6-(2,2,2-trifluoroethoxy)-1,3,5-triazin-2-ylamino)benzoic acid, In-1001

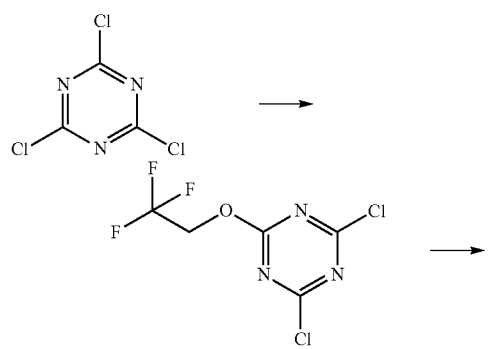

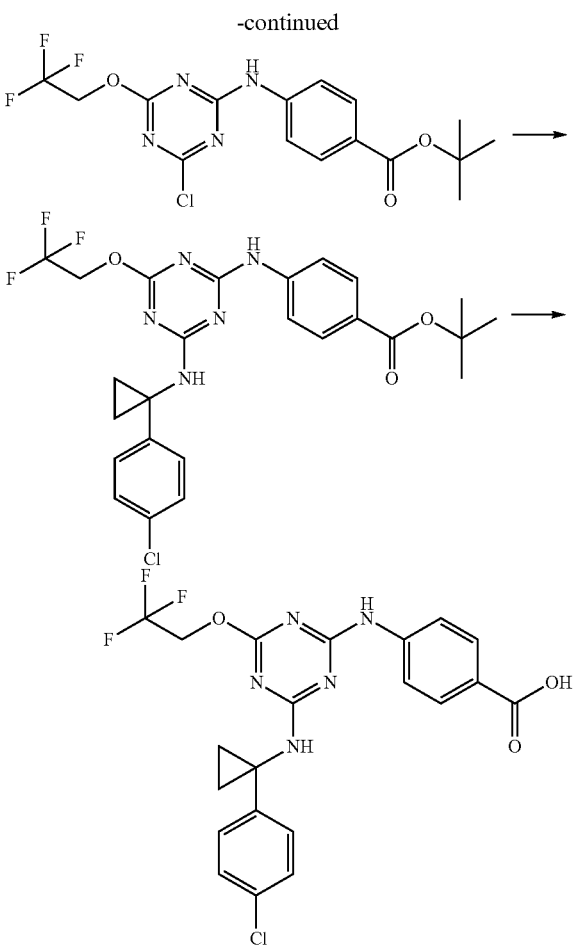

In-1001

Step 1:

To a solution of 2,4,6-trichloro-1,3,5-triazine (15 g) in THF (300 mL) was added 2,2,2-trifluoroethanol (8.14 g) and Hunig's Base (15.63 mL). The resulting mixture was stirred for 16 hours. After removal of most THF and precipitate through a plug washing with THF, the filtrate was concentrate to give a crude that will be used as it is.

Step 2:

To a solution of the product in Step 1 above (10 g) in THF (100 mL) was added tert-butyl 4-aminobenzoate (7.79 g) and Hunig's Base (7.04 mL). The resulting mixture was stirred for 16 h. The precipitate was filtered and washed with Et$_2$O, dried, then washed with water and dried to give 10.6 g of tert-butyl 4-(4-chloro-6-(2,2,2-trifluoroethoxy)-1,3,5-triazin-2-ylamino)benzoate as a solid.

| tert-butyl 4-(4-chloro-6-(2,2,2-trifluoroethoxy)-1,3,5-triazin-2-ylamino)benzoate | |
|---|---|
| MS (M + H)$^+$ Calcd. | 405.1 |
| MS (M + H)$^+$ Observ. | 405.0 |
| LC Condition | |
| Solvent A | 100% Water - 0.1% TFA |
| Solvent B | 100% ACN - 0.1% TFA |
| Start % B | 2 |
| Final % B | 98 |
| Gradient Time | 1.6 min |

-continued

| | |
|---|---|
| Stop Time | 1.8 min |
| Flow Rate | 0.8 mL/min |
| Wavelength | 220 |
| Solvent Pair | ACN -H₂0 - 0.1% TFA |
| Column | Aquity UPLC BEH C18 1.7 um |

Step 3:

To a slurry of tert-butyl 4-(4-chloro-6-(2,2,2-trifluoroethoxy)-1,3,5-triazin-2-ylamino)benzoate (3.6 g) and 1-(4-chlorophenyl)cyclopropanamine (1.49 g) in THF (50 mL) was stirred for 5 hours at 80° C. The precipitate was filtrated through a plug washing with THF to give acrude product that was purified by Biotage eluting with 4/1-hexane/ethyl acetate to give 1.8 g of tert-butyl 4-(4-(1-(4-chlorophenyl)cyclopropylamino)-6-(2,2,2-trifluoroethoxy)-1,3,5-triazin-2-ylamino)benzoate as a solid.

| tert-butyl 4-(4-(1-(4-chlorophenyl)cyclopropylamino)-6-(2,2,2-trifluoroethoxy)-1,3,5-triazin-2-ylamino)benzoate | |
|---|---|
| MS (M + H)⁺ Calcd. | 536.2 |
| MS (M + H)⁺ Observ. | 536.0 |
| LC Condition | |
| Solvent A | 100% Water - 0.1% TFA |
| Solvent B | 100% ACN - 0.1% TFA |
| Start % B | 2 |
| Final % B | 98 |
| Gradient Time | 1.6 min |
| Stop Time | 1.8 min |
| Flow Rate | 0.8 mL/min |
| Wavelength | 220 |
| Solvent Pair | ACN -H₂0 - 0.1% TFA |
| Column | Aquity UPLC BEH C18 1.7 um |

Step 4:

A solution of above tert-butyl 4-(4-(1-(4-chlorophenyl)cyclopropylamino)-6-(2,2,2-trifluoroethoxy)-1,3,5-triazin-2-ylamino)benzoate (4 g) and HCl in dioxane (7.46 ml, 4M) was stirred for 4 hours. Concentration gave 3.58 g of 4-(4-(1-(4-chlorophenyl)cyclopropylamino)-6-(2,2,2-trifluoroethoxy)-1,3,5-triazin-2-ylamino)benzoic acid as a solid.

| 4-(4-(1-(4-chlorophenyl)cyclopropylamino)-6-(2,2,2-trifluoroethoxy)-1,3,5-triazin-2-ylamino)benzoic acid, In-1001 | |
|---|---|
| MS (M + H)⁺ Calcd. | 480.1 |
| MS (M + H)⁺ Observ. | 480.1 |
| LC Condition | |
| Solvent A | 100% Water - 0.1% TFA |
| Solvent B | 100% ACN - 0.1% TFA |
| Start % B | 2 |
| Final % B | 98 |
| Gradient Time | 1.6 min |
| Stop Time | 1.8 min |
| Flow Rate | 0.8 mL/min |
| Wavelength | 220 |
| Solvent Pair | ACN -H₂0 - 0.1% TFA |
| Column | Aquity UPLC BEH C18 1.7 um |

Preparation of Intermediate 1002

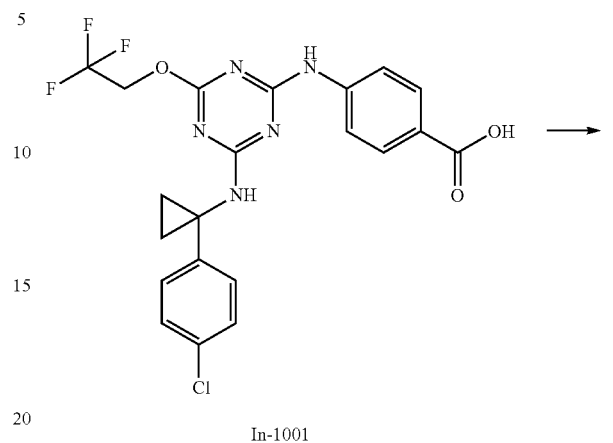

In-1001

In-1002

2-(3H-[1,2,3]triazolo[4,5-b]pyridin-3-yl)-1,1,3,3-tetramethylisouronium hexafluorophosphate(V) (0.317 g) and iPr₂NEt (0.215 g) were added into a solution of Compound In-1001 (0.40 g) and tert-butyl 2,7-diazaspiro[4.4]nonane-2-carboxylate (0.189 g) in DMF (2 mL) and the reaction was stirred at room temperature for 1 hour. The Compound 1002 was isolated using preparative HPLC.

| In-1002 | |
|---|---|
| MS (M + H)⁺ Calcd. | 688.3 |
| MS (M + H)⁺ Observ. | 688.3 |
| Retention Time | 3.61 min |
| LC Condition | |
| Solvent A | 5% ACN:95% Water: 10 mM Ammonium Actetate |
| Solvent B | 95% ACN:5% Water: 10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water: Ammonium Actetate |
| Column | Phenomenex LUNA C18, 50 × 2, 3 u |

Preparation of Intermediate 1003

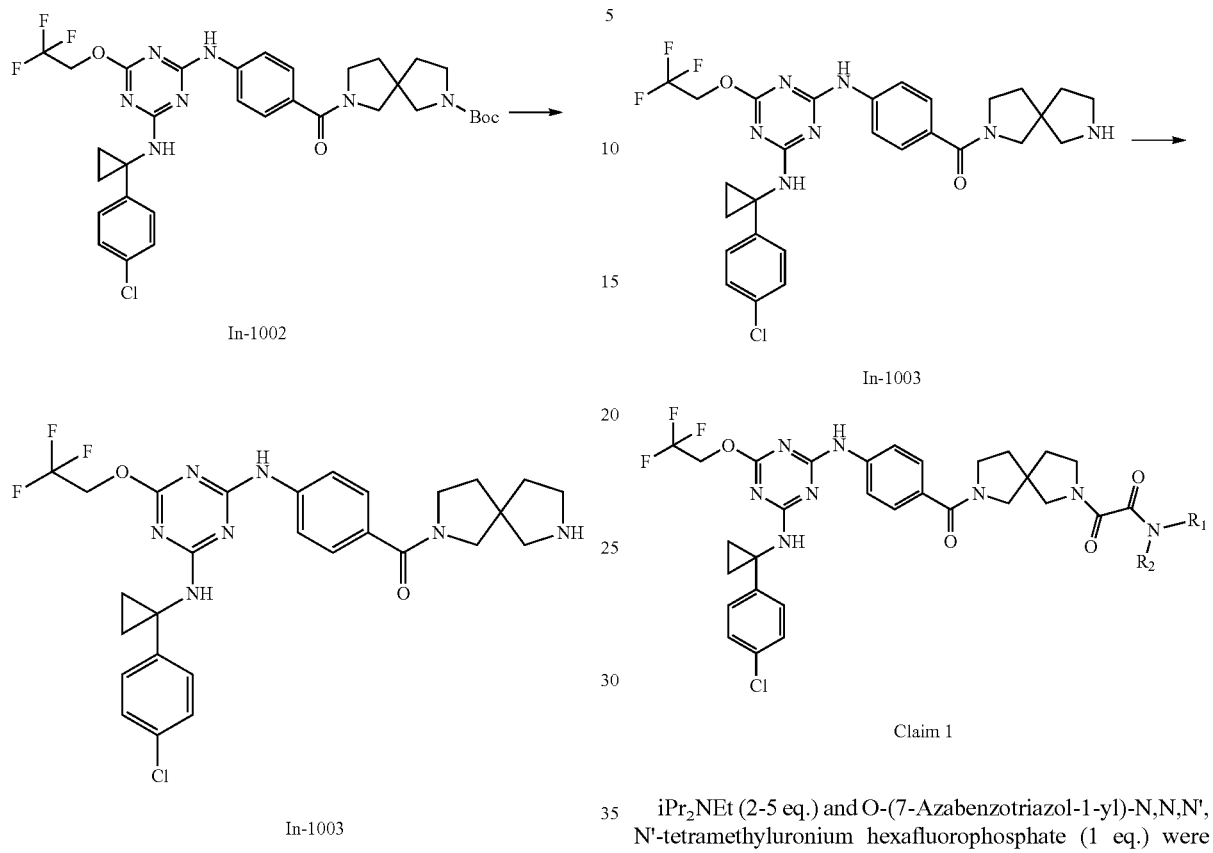

In-1002

In-1003

TFA (0.59 mL) was added into a solution of Compound In-1002 (0.35 g) in CH$_2$Cl$_2$ (1 mL) and the reaction was stirred at room temperature for 16 hours. After removal of solvents under vacuum, the residue was purified using preparative HPLC.

| In-1003 | |
| --- | --- |
| MS (M + H)$^+$ Calcd. | 588.2 |
| MS (M + H)$^+$ Observ. | 588.2 |
| Retention Time | 3.72 min |
| LC Condition | |
| Solvent A | 5:95 methanol:water with 10 mM ammonium acetate |
| Solvent B | 95:5 methanol:water with 10 mM ammonium acetate |
| Gradient | 0.5 min hold at 0% B, 0-100% B over 4 minutes, then a 0.5-minute hold at 100% B |
| Flow Rate | 0.5 mL/min |
| Wavelength | 220 |
| Solvent Pair | Water - Methanol- TFA |
| Column | Waters BEH C18, 2.0 × 50 mm, 1.7-μm particles |

General Procedure for the Preparation of Compounds 1001-1015

In-1003

Claim 1 iPr$_2$NEt (2-5 eq.) and O-(7-Azabenzotriazol-1-yl)-N,N,N',N'-tetramethyluronium hexafluorophosphate (1 eq.) were added into a solution of In-1003 (15 mg, 1 eq.) and amino (oxo)acetic acid (1 eq.) in DMF (1 mL). The reaction was stirred at room temperature for 1-16 hours. The product was then isolated by preparative HPLC.

| LC Condition A | |
| --- | --- |
| Solvent A | 5% ACN:95% Water: 10 mM Ammonium Actetate |
| Solvent B | 95% ACN:5% Water: 10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water: Ammonium Actetate |
| Column | Phenomenex LUNA C18, 30 × 2, 3 u |

| LC Condition B | |
| --- | --- |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

| Cmpd # | Structure | MS (M + H)+ Calcd. | MS (M + H)+ Observ. | Retention Time (min) | LC Condition |
|---|---|---|---|---|---|
| 1001 | 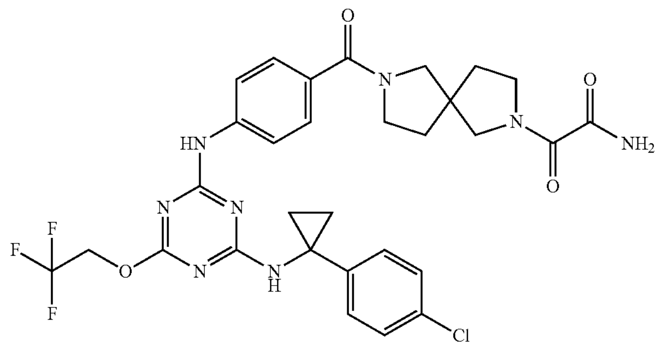 [SMILES: NC(=O)C(=O)N1CCC2(CCN(C(=O)c3ccc(Nc4nc(NC5(c6ccc(Cl)cc6)CC5)nc(OCC(F)(F)F)n4)cc3)C2)C1] | 659.2 | 659.1 | 1.63 | A |
| 1002 | 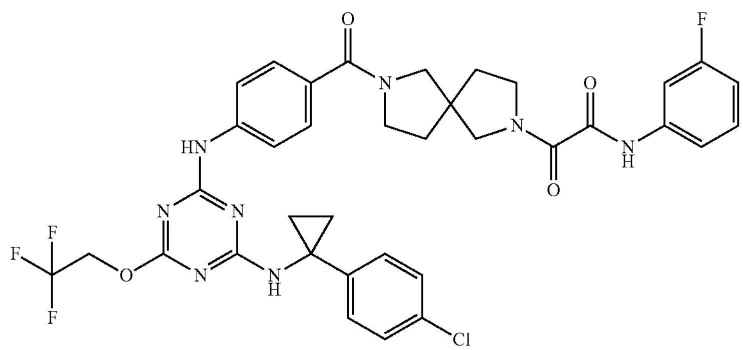 [SMILES: O=C(Nc1cccc(F)c1)C(=O)N1CCC2(CCN(C(=O)c3ccc(Nc4nc(NC5(c6ccc(Cl)cc6)CC5)nc(OCC(F)(F)F)n4)cc3)C2)C1] | 753.2 | 753.2 | 1.93 | A |
| 1003 | 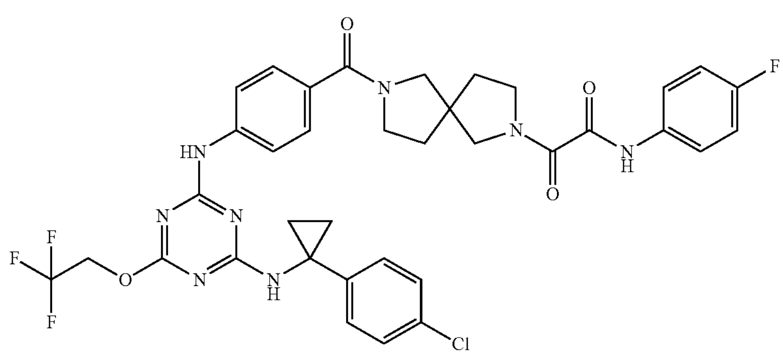 [SMILES: O=C(Nc1ccc(F)cc1)C(=O)N1CCC2(CCN(C(=O)c3ccc(Nc4nc(NC5(c6ccc(Cl)cc6)CC5)nc(OCC(F)(F)F)n4)cc3)C2)C1] | 753.2 | 753.4 | 2.35 | B |
| 1004 | 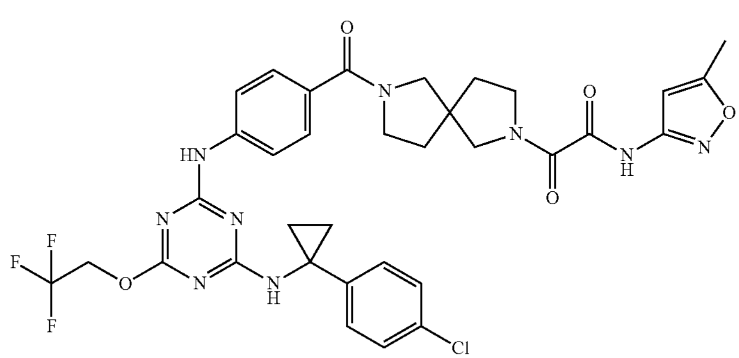 [SMILES: Cc1cc(NC(=O)C(=O)N2CCC3(CCN(C(=O)c4ccc(Nc5nc(NC6(c7ccc(Cl)cc7)CC6)nc(OCC(F)(F)F)n5)cc4)C3)C2)no1] | 740.2 | 740.2 | 1.81 | A |

-continued
| Cmpd # | Structure | MS (M + H)+ Calcd. | MS (M + H)+ Observ. | Retention Time (min) | LC Condition |
|---|---|---|---|---|---|
| 1005 | 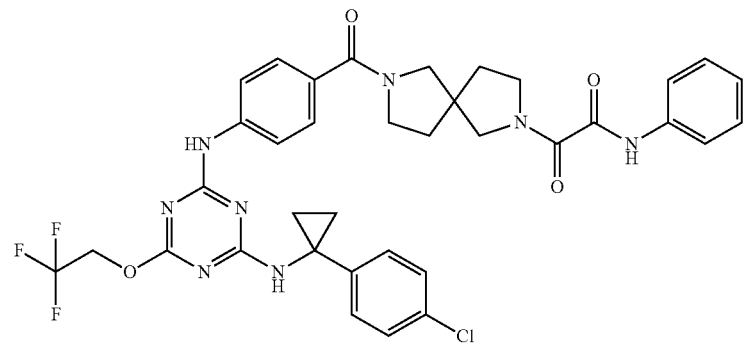 [SMILES: O=C(Nc1ccccc1)C(=O)N1CCC2(CCN(C(=O)c3ccc(Nc4nc(NC5(c6ccc(Cl)cc6)CC5)nc(OCC(F)(F)F)n4)cc3)C2)C1] | 735.2 | 735.4 | 2.34 | B |
| 1006 | 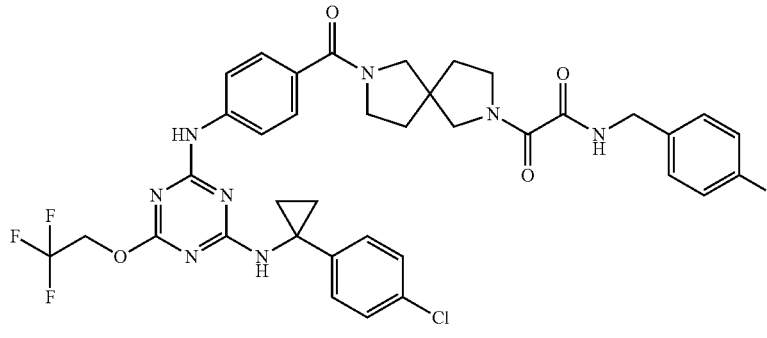 | 767.2 | 767.4 | 2.32 | B |
| 1007 | 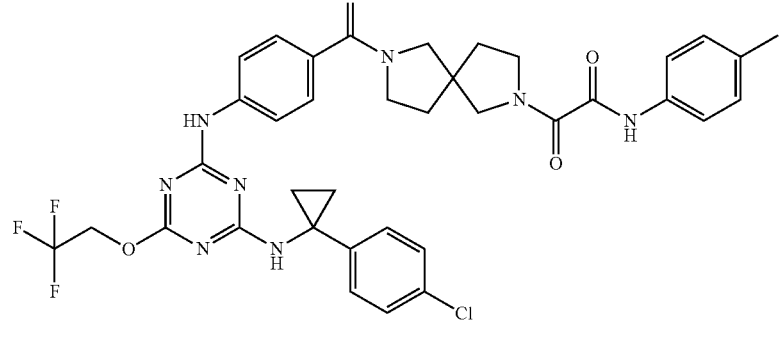 | 749.3 | 749.4 | 2.39 | B |
| 1008 | 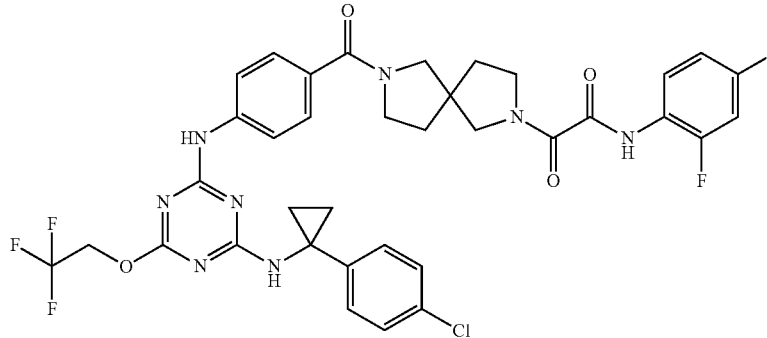 | 771.2 | 771.2 | 1.95 | A |

-continued
| Cmpd # | Structure | MS (M + H)+ Calcd. | MS (M + H)+ Observ. | Retention Time (min) | LC Condition |
|---|---|---|---|---|---|
| 1009 | 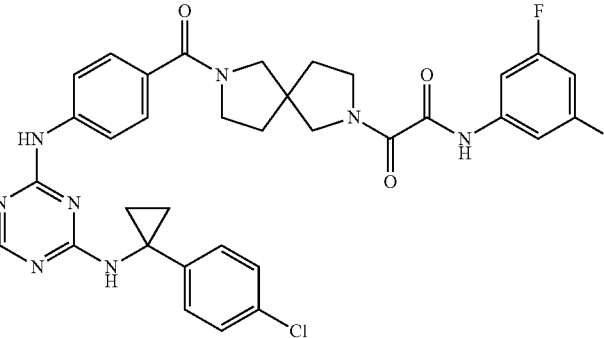 | 771.2 | 771.3 | 2.10 | A |
| 1010 | 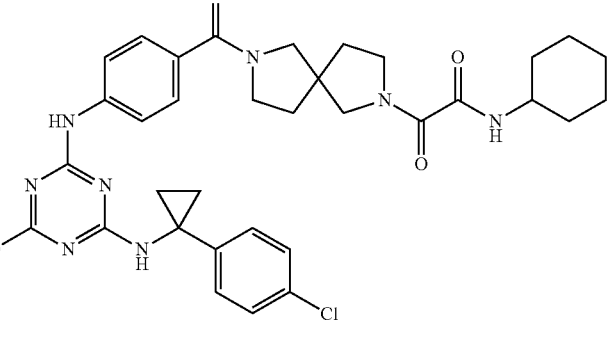 | 741.3 | 741.3 | 1.92 | A |
| 1011 | 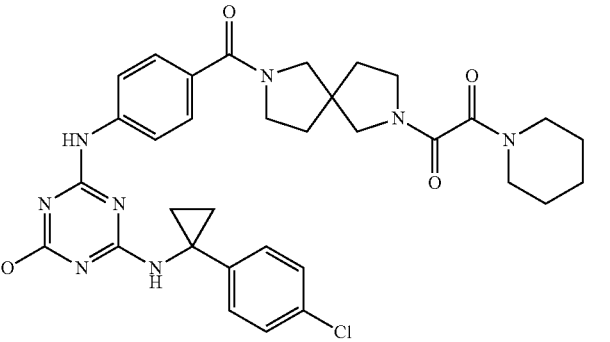 | 727.3 | 727.4 | 2.23 | B |
| 1012 | 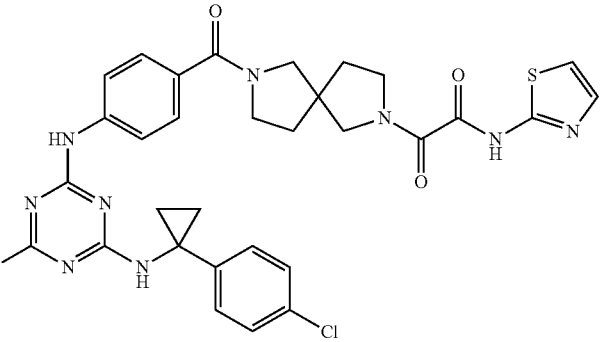 | 742.2 | 742.2 | 1.80 | A |

| Cmpd # | Structure | MS (M + H)+ Calcd. | MS (M + H)+ Observ. | Retention Time (min) | LC Condition |
|---|---|---|---|---|---|
| 1013 | 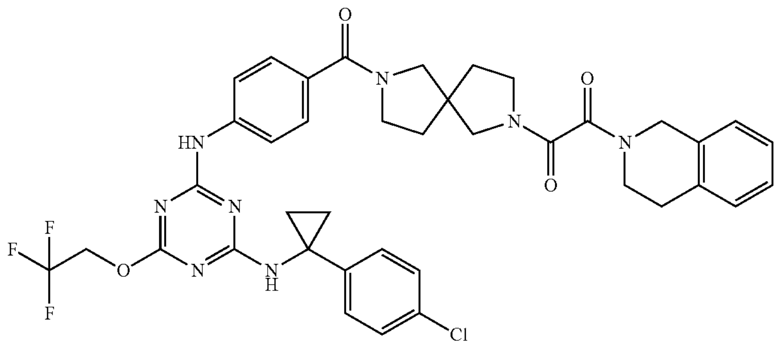 [SMILES: O=C(C(=O)N1CCC2(CCN(C(=O)c3ccc(Nc4nc(NC5(c6ccc(Cl)cc6)CC5)nc(OCC(F)(F)F)n4)cc3)C2)C1)N1CCc2ccccc2C1] | 775.3 | 775.5 | 2.29 | B |
| 1014 | 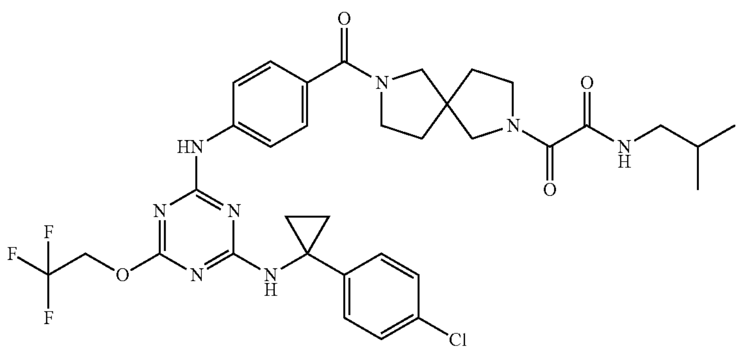 [SMILES: CC(C)CNC(=O)C(=O)N1CCC2(CCN(C(=O)c3ccc(Nc4nc(NC5(c6ccc(Cl)cc6)CC5)nc(OCC(F)(F)F)n4)cc3)C2)C1] | 715.3 | 715.4 | 2.31 | B |
| 1015 | 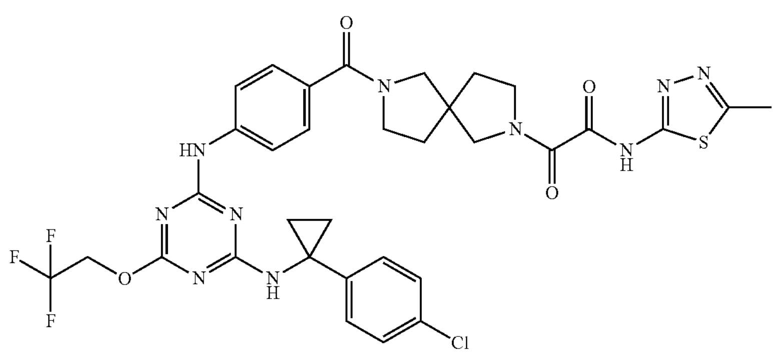 [SMILES: Cc1nnc(NC(=O)C(=O)N2CCC3(CCN(C(=O)c4ccc(Nc5nc(NC6(c7ccc(Cl)cc7)CC6)nc(OCC(F)(F)F)n5)cc4)C3)C2)s1] | 757.2 | 757.4 | 2.24 | B |

Biological Methods

Infection Assays.

HCV pseudoparticles, produced using standardized methodology (Bartosch, B., Dubuisson, J. and Cosset, F.-L. *J. Exp. Med.* 2003, 197:633-642) were made via a liposome-based transfection procedure of 293T cells with plasmids expressing the murine leukemia virus capsid and polymerase proteins, an MLV genome encoding the luciferase reporter gene, and envelope glycoproteins from either HCV or vesicular stomatitis virus (VSV). The genotype 1a HCV E1 and E2 envelope coding sequences were derived from the H77C isolate (GenBank accession number AF009606). Media containing pseudoparticles was collected 3 days following transfection, filtered, and stored at −20° C. as a viral stock. Infections were performed in 384-well plates by mixing pseudovirus with $1 \times 10^4$ Huh7 cells/well in the presence or absence of test inhibitors, followed by incubation at 37° C. Luciferase activity, reflecting the degree of entry of the pseudoparticles into host cells, was measured 2 days after infection. The specificity of the compounds for inhibiting HCV was determined by evaluating inhibition of VSV pseudoparticle infection.

Compounds and Data Analysis.

Test compounds were serially diluted 3-fold in dimethyl sulfoxide (DMSO) to give a final concentration range in the assay of 50.0 µM to 0.04 µM. Maximum activity (100% of control) and background were derived from control wells containing DMSO but no inhibitor or from uninfected wells, respectively. The individual signals in each of the compound test wells were then divided by the averaged control values after background subtraction and multiplied by 100% to determine percent activity. Assays were performed in duplicate and average $EC_{50}$ values (reflecting the concentration at which 50% inhibition of virus replication was achieved) were calculated. Compound $EC_{50}$ data is expressed as A=0.01≤10 nM; B=10-1000 nM. Representative data for compounds are reported in Table 2.

TABLE 2

| Cmpd # | Structure | EC$_{50}$ (nM) 1a (H77C) | EC$_{50}$ (nM) 1a (H77C) |
|---|---|---|---|
| 1001 | 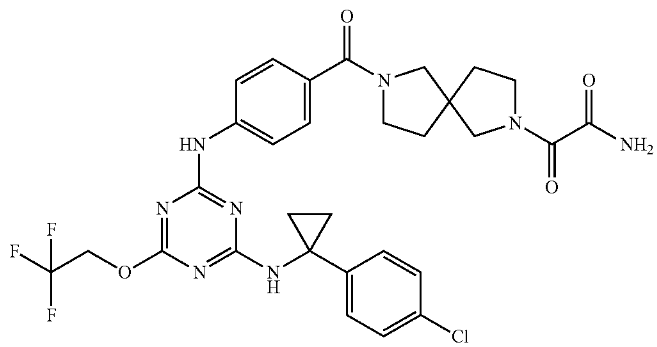 [SMILES: NC(=O)C(=O)N1CCC2(CCN(C(=O)c3ccc(Nc4nc(NC5(c6ccc(Cl)cc6)CC5)nc(OCC(F)(F)F)n4)cc3)C2)C1] | A | 1.639 |
| 1002 | 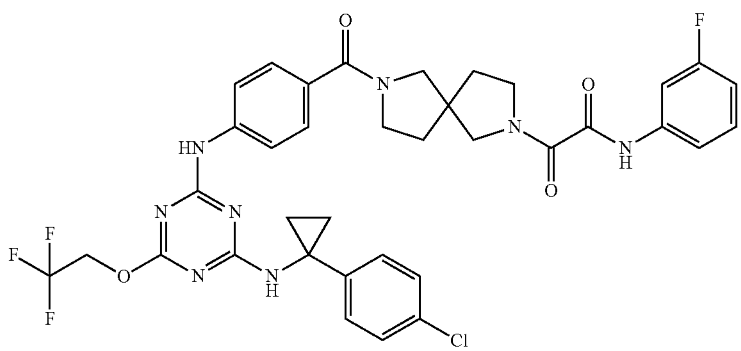 [SMILES: O=C(Nc1cccc(F)c1)C(=O)N1CCC2(CCN(C(=O)c3ccc(Nc4nc(NC5(c6ccc(Cl)cc6)CC5)nc(OCC(F)(F)F)n4)cc3)C2)C1] | A | |
| 1003 | 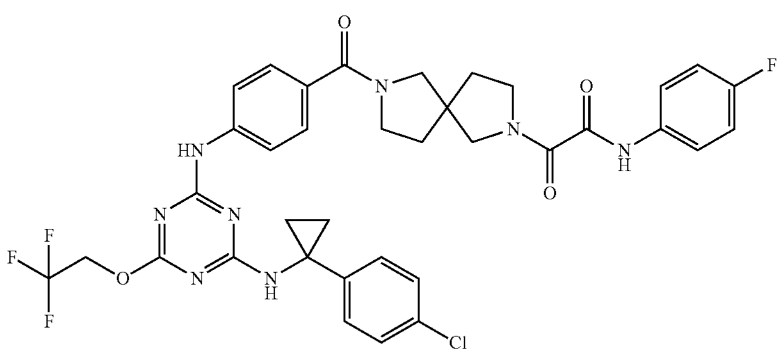 [SMILES: O=C(Nc1ccc(F)cc1)C(=O)N1CCC2(CCN(C(=O)c3ccc(Nc4nc(NC5(c6ccc(Cl)cc6)CC5)nc(OCC(F)(F)F)n4)cc3)C2)C1] | A | |
| 1004 | 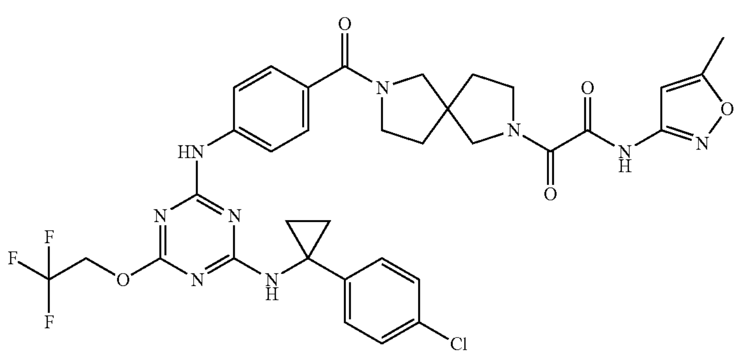 [SMILES: Cc1cc(NC(=O)C(=O)N2CCC3(CCN(C(=O)c4ccc(Nc5nc(NC6(c7ccc(Cl)cc7)CC6)nc(OCC(F)(F)F)n5)cc4)C3)C2)no1] | A | |

TABLE 2-continued

| Cmpd # | Structure | EC$_{50}$ (nM) 1a (H77C) | EC$_{50}$ (nM) 1a (H77C) |
|---|---|---|---|
| 1005 | 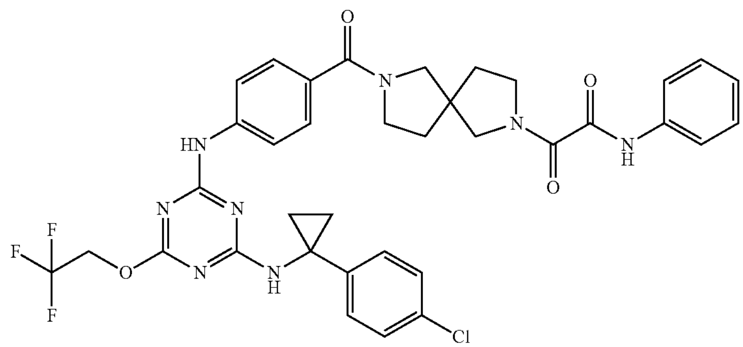 [SMILES: O=C(Nc1ccccc1)C(=O)N1CCC2(CCN(C(=O)c3ccc(Nc4nc(NC5(c6ccc(Cl)cc6)CC5)nc(OCC(F)(F)F)n4)cc3)C2)C1] | A | |
| 1006 | 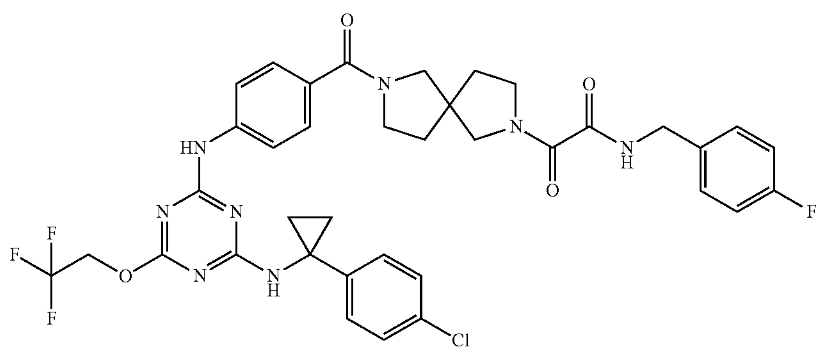 [SMILES: O=C(NCc1ccc(F)cc1)C(=O)N1CCC2(CCN(C(=O)c3ccc(Nc4nc(NC5(c6ccc(Cl)cc6)CC5)nc(OCC(F)(F)F)n4)cc3)C2)C1] | A | |
| 1007 | 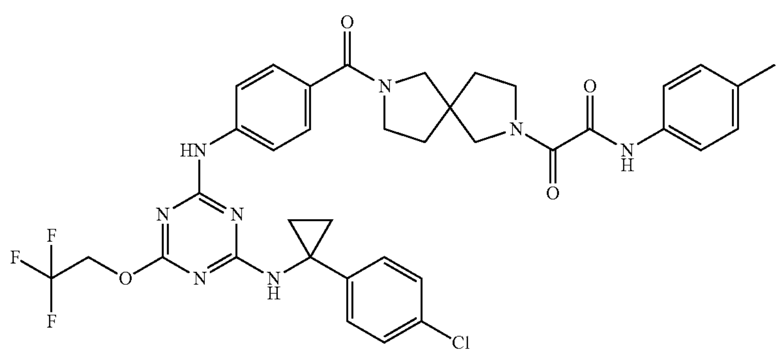 [SMILES: Cc1ccc(NC(=O)C(=O)N2CCC3(CCN(C(=O)c4ccc(Nc5nc(NC6(c7ccc(Cl)cc7)CC6)nc(OCC(F)(F)F)n5)cc4)C3)C2)cc1] | A | 0.2552 |
| 1008 | 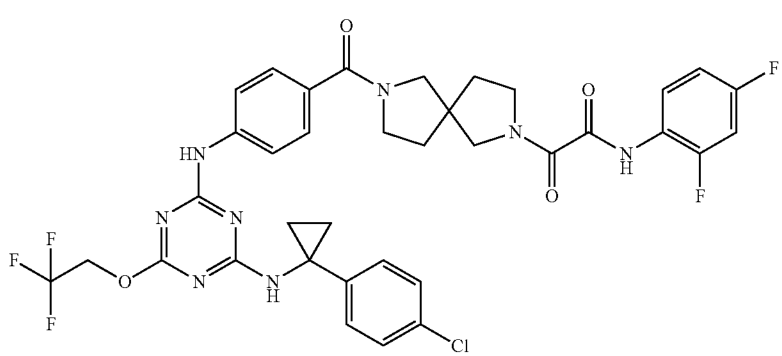 [SMILES: O=C(Nc1ccc(F)cc1F)C(=O)N1CCC2(CCN(C(=O)c3ccc(Nc4nc(NC5(c6ccc(Cl)cc6)CC5)nc(OCC(F)(F)F)n4)cc3)C2)C1] | A | |

TABLE 2-continued

| Cmpd # | Structure | EC$_{50}$ (nM) 1a (H77C) | EC$_{50}$ (nM) 1a (H77C) |
|---|---|---|---|
| 1009 | 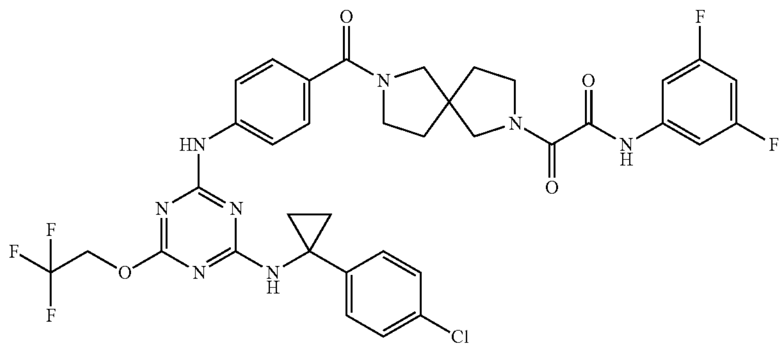 [SMILES: O=C(Nc1cc(F)cc(F)c1)C(=O)N1CCC2(CCN(C(=O)c3ccc(Nc4nc(NC5(c6ccc(Cl)cc6)CC5)nc(OCC(F)(F)F)n4)cc3)C2)C1] | | A |
| 1010 | 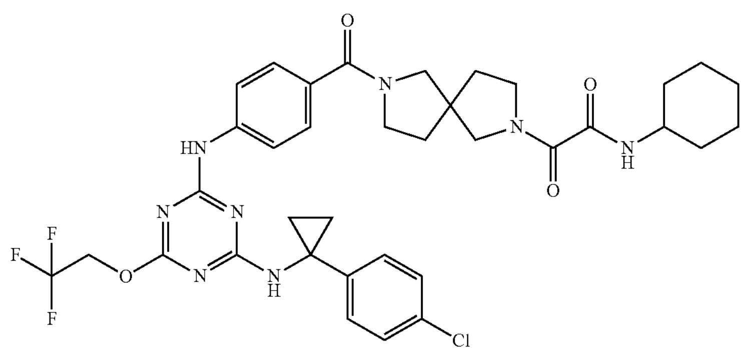 [SMILES: O=C(NC1CCCCC1)C(=O)N1CCC2(CCN(C(=O)c3ccc(Nc4nc(NC5(c6ccc(Cl)cc6)CC5)nc(OCC(F)(F)F)n4)cc3)C2)C1] | | A |
| 1011 | 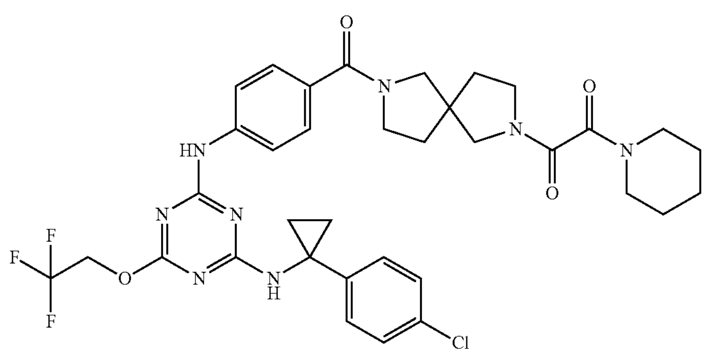 [SMILES: O=C(C(=O)N1CCC2(CCN(C(=O)c3ccc(Nc4nc(NC5(c6ccc(Cl)cc6)CC5)nc(OCC(F)(F)F)n4)cc3)C2)C1)N1CCCCC1] | | A |
| 1012 | 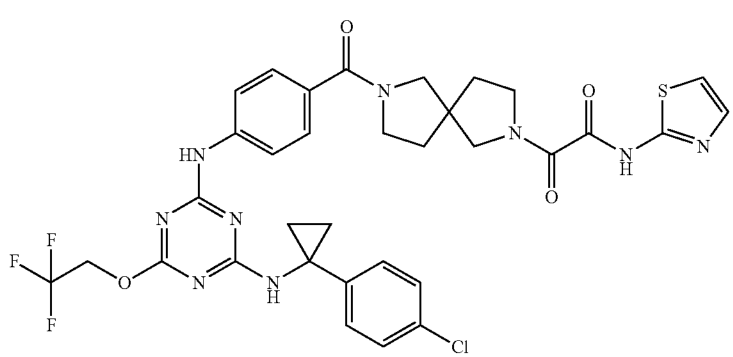 [SMILES: O=C(Nc1nccs1)C(=O)N1CCC2(CCN(C(=O)c3ccc(Nc4nc(NC5(c6ccc(Cl)cc6)CC5)nc(OCC(F)(F)F)n4)cc3)C2)C1] | | A |

TABLE 2-continued

| Cmpd # | Structure | EC$_{50}$ (nM) 1a (H77C) | EC$_{50}$ (nM) 1a (H77C) |
|---|---|---|---|
| 1013 | 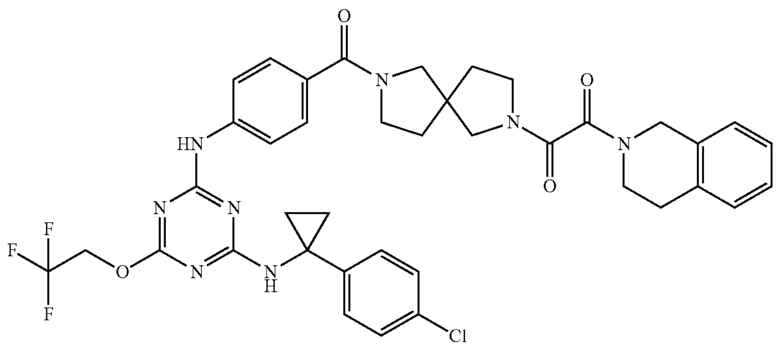 [SMILES: O=C(C(=O)N1CCC2(CCN(C(=O)c3ccc(Nc4nc(NC5(c6ccc(Cl)cc6)CC5)nc(OCC(F)(F)F)n4)cc3)C2)C1)N1CCc2ccccc2C1] | A | 4.864 |
| 1014 | 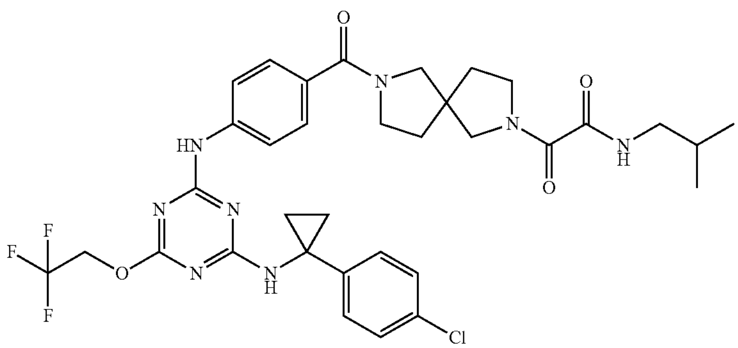 [SMILES: CC(C)CNC(=O)C(=O)N1CCC2(CCN(C(=O)c3ccc(Nc4nc(NC5(c6ccc(Cl)cc6)CC5)nc(OCC(F)(F)F)n4)cc3)C2)C1] | A | |
| 1015 | 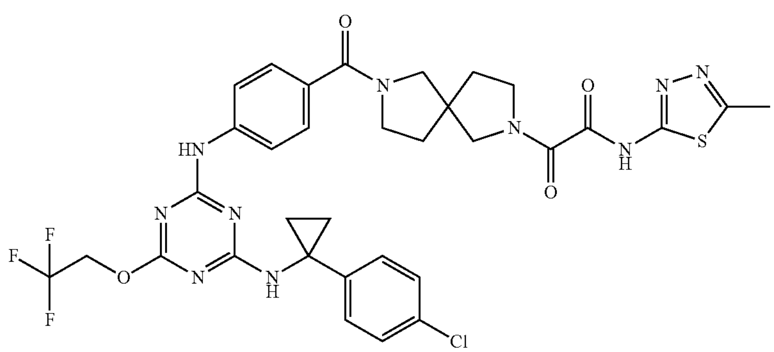 [SMILES: Cc1nnc(NC(=O)C(=O)N2CCC3(CCN(C(=O)c4ccc(Nc5nc(NC6(c7ccc(Cl)cc7)CC6)nc(OCC(F)(F)F)n5)cc4)C3)C2)s1] | A | |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I, and pharmaceutically acceptable salts thereof:

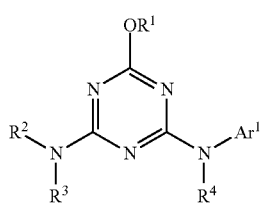

I wherein

R$^1$ is selected from alkyl, hydroxyalkyl, alkoxyalkyl, haloalkyl, cycloalkyl, hydroxycycloalkyl, alkoxycycloalkyl, halocycloalkyl, cycloalkenyl, indanyl, alkylcarbonyl, and benzyl, wherein the benzyl moiety is substituted with 0-3 substituents selected from halo, alkyl, haloalkyl, alkoxy, and haloalkoxy;

$R^2$ is selected from alkyl, $(Ar^2)$alkyl, $(Ar^2)$cycloalkyl, $((Ar^2)$cycloalkyl)alkyl, $((Ar^2)$alkyl)cycloalkyl, and $(((Ar^2)$alkyl)cycloalkyl)alkyl;

$R^3$ is hydrogen or alkyl;

$R^4$ is hydrogen or alkyl;

$R^5$ is selected from

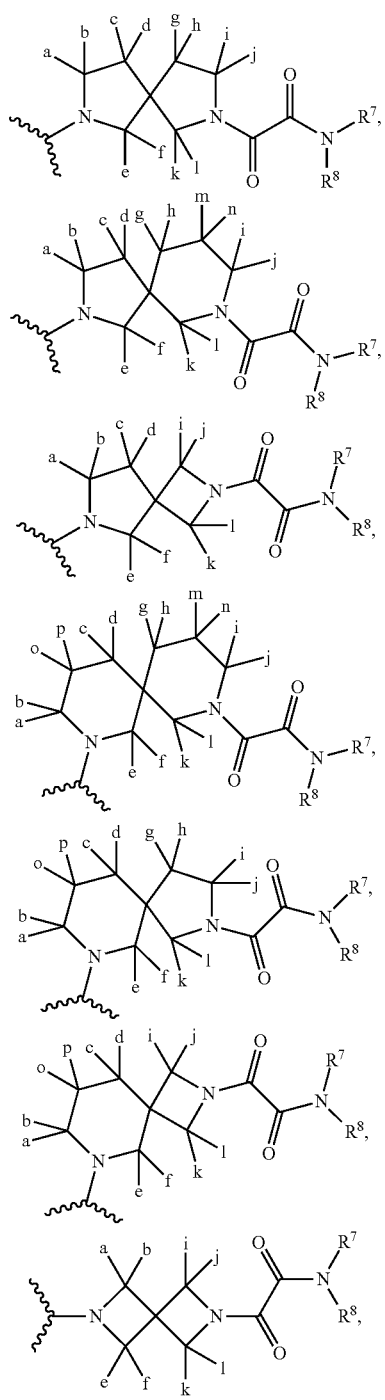

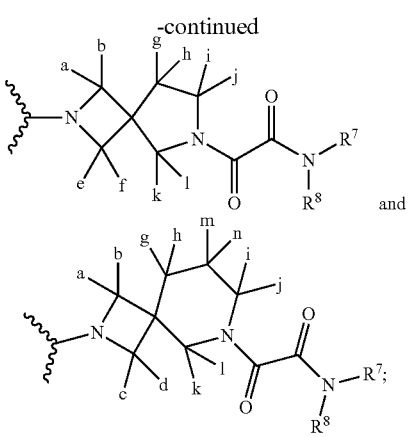

$R^6$ is selected from halo, alkyl, haloalkyl, alkoxy, and haloalkoxy;

$R^7$ is selected from alkyl, cycloalkyl, (cycloalkyl)alkyl, (alkyl)cycloalkyl, ((alkyl))cycloalkyl)alkyl, and a bridged bicycloalkyl, and is substituted with 0-4 substituents selected from halo, alkyl, cycloalkyl, hydroxyalkyl, alkoxyalkyl, hydroxy, alkoxy, benzyloxy, $CO_2R^9$, $N(R^{10})(R^{11})$, tetrahydrofuranyl, tetrahydropyranyl, and $Ar^4$;

or $R^7$ is hydrogen, N-alkoxycarbonylpiperidinyl, piperidinonyl, or $Ar^3$;

$R^8$ is hydrogen or alkyl;

or $R^7$ and $R^8$ taken together with the nitrogen to which they are attached is selected from azetidinyl, pyrrolidinyl, piperidinyl, piperazinyl, and morpholinyl, and is substituted with 0-2 substituents selected from alkyl, alkylcarbonyl, and alkoxycarbonyl;

$R^9$ is selected from hydrogen, alkyl, hydroxyalkyl, alkoxyalkyl, ((hydroxyalkyl)alkoxy)alkoxy, and ((alkoxy)alkoxy)alkoxy;

$R^{10}$ is selected from hydrogen, alkyl, cycloalkyl, alkylcarbonyl, and alkoxycarbonyl;

$R^{11}$ is hydrogen or alkyl;

or $R^{10}$ and $R^{11}$ taken together with the nitrogen to which they are attached is selected from azetidinyl, pyrrolidinyl, piperidinyl, piperazinyl, and morpholinyl, and is substituted with 0-2 substituents selected from alkyl, alkylcarbonyl, and alkoxycarbonyl;

$R^{12}$ is hydrogen or alkyl;

$R^{13}$ is selected from hydrogen, alkyl, cycloalkyl, alkylcarbonyl, and alkoxycarbonyl;

$R^{14}$ is hydrogen or alkyl;

or $R^{13}$ and $R^{14}$ taken together with the nitrogen to which they are attached is selected from azetidinyl, pyrrolidinyl, piperidinyl, piperazinyl, and morpholinyl, and is substituted with 0-2 substituents selected from alkyl, alkylcarbonyl, and alkoxycarbonyl;

$Ar^1$ is phenyl substituted with 1 $CO(R^5)$ and with 0-3 substituents selected from $R^6$;

$Ar^2$ is phenyl substituted with 0-3 substituents selected from halo, alkyl, haloalkyl, alkoxy, and haloalkoxy;

$Ar^3$ is selected from phenyl, indanyl, fluorenyl, biphenyl, terphenyl, pyridinyl, pyrazolyl, isoxazolyl, imidazolyl, thiazolyl, thiadiazolyl, triazolyl, benzoxazolyl, indolinyl, and dibenzofuranyl, and is substituted with 0-3 substituents selected from cyano, halo, alkyl, alkenyl, haloalkyl, cycloalkyl, $(CO_2R^{12})$alkyl, $(CO_2R^{12})$alkenyl, (CON($R^{13}$)($R^{14}$))alkyl, phenyl, hydroxy, alkoxy, haloalkoxy, alkylcarbonyl, $CO_2R^{12}$, CON($R^{13}$)($R^{14}$), and PhCONHSO$_2$;

or Ar$^3$ is phenyl substituted with 1 substituent selected from benzyl, tetrazolyloxy, thiazolyl, phenylpyrazolyl, methyloxadiazolyl, thiadiazolyl, triazolyl, methyltriazolyl, tetrazolyl, pyridinyl, and dimethoxypyrimidinyl;

Ar$^4$ is selected from phenyl, indanyl, tetrahydronaphthyl, isochromanyl, benzodioxolyl, pyridinyl, pyrazolyl, imidazolyl, and triazolyl, and is substituted with 0-3 substituents selected from cyano, halo, alkyl, alkenyl, haloalkyl, alkoxy, haloalkoxy, N($R^{13}$)($R^{14}$), and alkylCO; and wherein a, b, c, d, e, f, g, h, i, j, k, l, m, n, o, and p are each independently hydrogen, alkyl, or cycloalkyl.

2. The compound of claim 1 wherein $R^1$ is haloalkyl.

3. The compound of claim 2 wherein $R^1$ is trifluoroethyl.

4. The compound of claim 1 wherein $R^1$ is haloalkyl; $R^2$ is (Ar$^2$)alkyl or (Ar$^2$)cycloalkyl; $R^3$ is hydrogen; $R^4$ is hydrogen; $R^7$ is alkyl, cycloalkyl, (cycloalkyl)alkyl, (alkyl)cycloalkyl, ((alkyl))cycloalkyl)alkyl, or a bridged bicycloalkyl, and is substituted with 0-4 substituents selected from halo, alkyl, cycloalkyl, hydroxyalkyl, alkoxyalkyl, hydroxy, alkoxy, benzyloxy, $CO_2R^9$, N($R^{10}$)($R^{11}$), tetrahydrofuranyl, tetrahydropyranyl, and Ar$^4$; or $R^7$ is Ar$^3$; and Ar$^1$ is phenyl para-substituted with 1 CO($R^5$).

5. The compound of claim 1 wherein $R^2$ is (Ar$^2$)alkyl or (Ar$^2$)cycloalkyl.

6. The compound of claim 1 wherein $R^3$ is hydrogen and $R^4$ is hydrogen.

7. The compound of claim 1 wherein $R^7$ is Ar$^3$.

8. The compound of claim 1 wherein Ar$^1$ is phenyl para-substituted with 1 CO($R^5$).

9. The compound of claim 1 wherein $R^7$ is alkyl, cycloalkyl, (cycloalkyl)alkyl, (alkyl)cycloalkyl, ((alkyl))cycloalkyl)alkyl, or a bridged bicycloalkyl, and is substituted with 0-4 substituents selected from halo, alkyl, cycloalkyl, hydroxyalkyl, alkoxyalkyl, hydroxy, alkoxy, benzyloxy, $CO_2R^9$, N($R^{10}$)($R^{11}$), tetrahydrofuranyl, tetrahydropyranyl, and Ar$^4$.

10. The compound of claim 4 or 9 wherein $R^5$ is

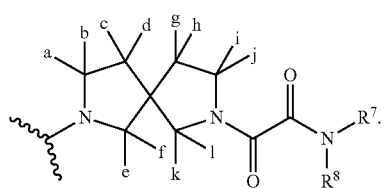

11. A pharmaceutical composition comprising one or more compounds of claim 1, and a pharmaceutically acceptable carrier.

12. A method of treating hepatitis C infection in a patient comprising administering to said patient a therapeutically effective amount of a compound of claim 1.

13. The compound, and pharmaceutically acceptable salts thereof, which is selected from the group of

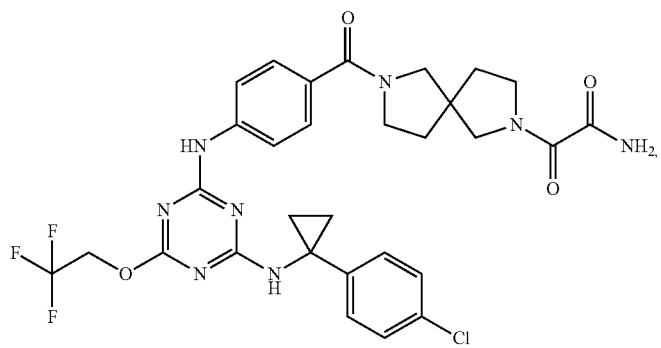

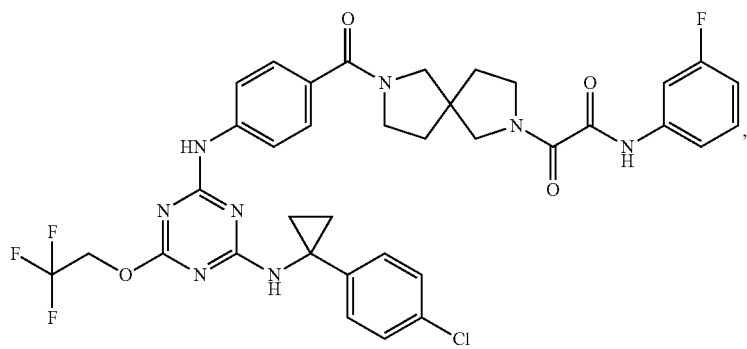

-continued
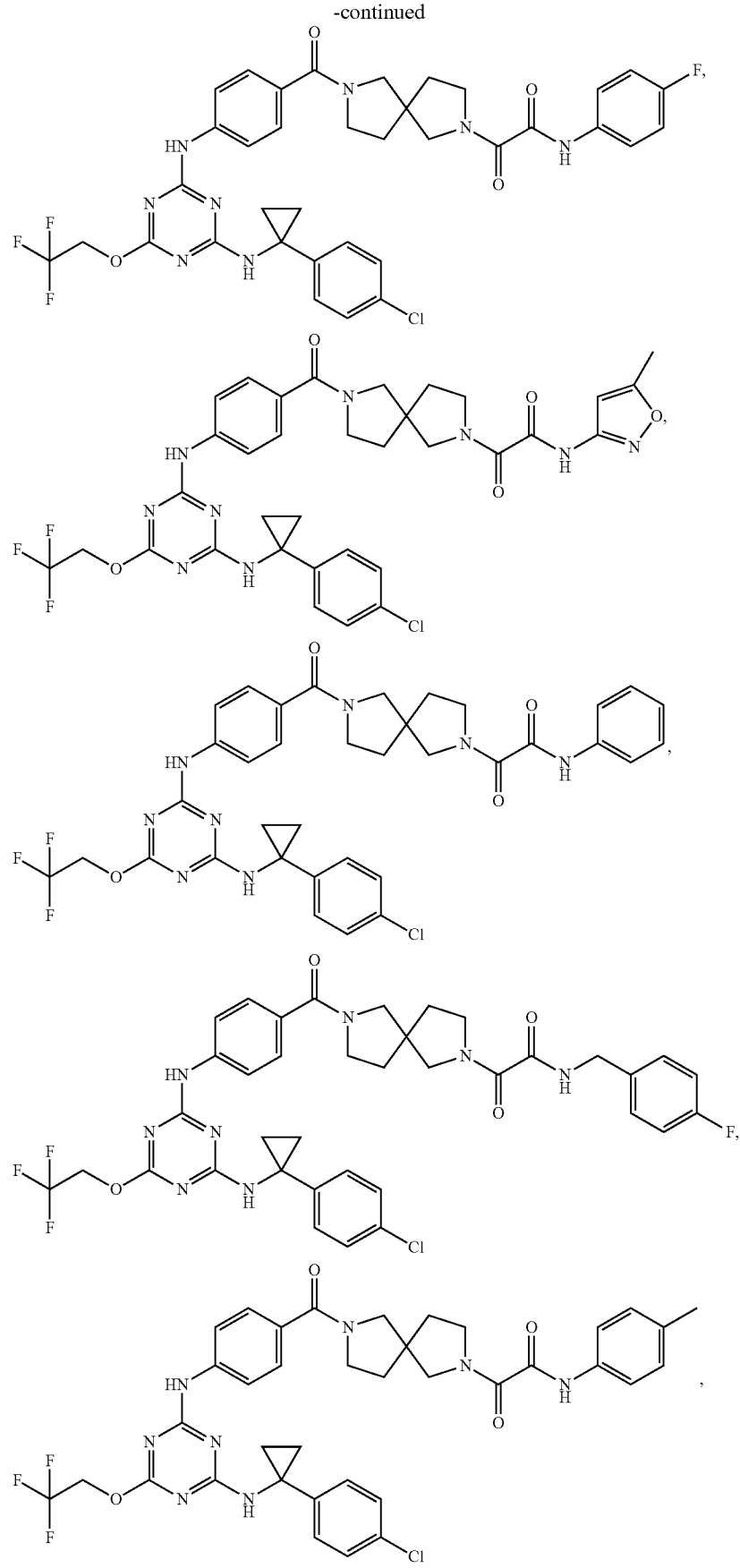

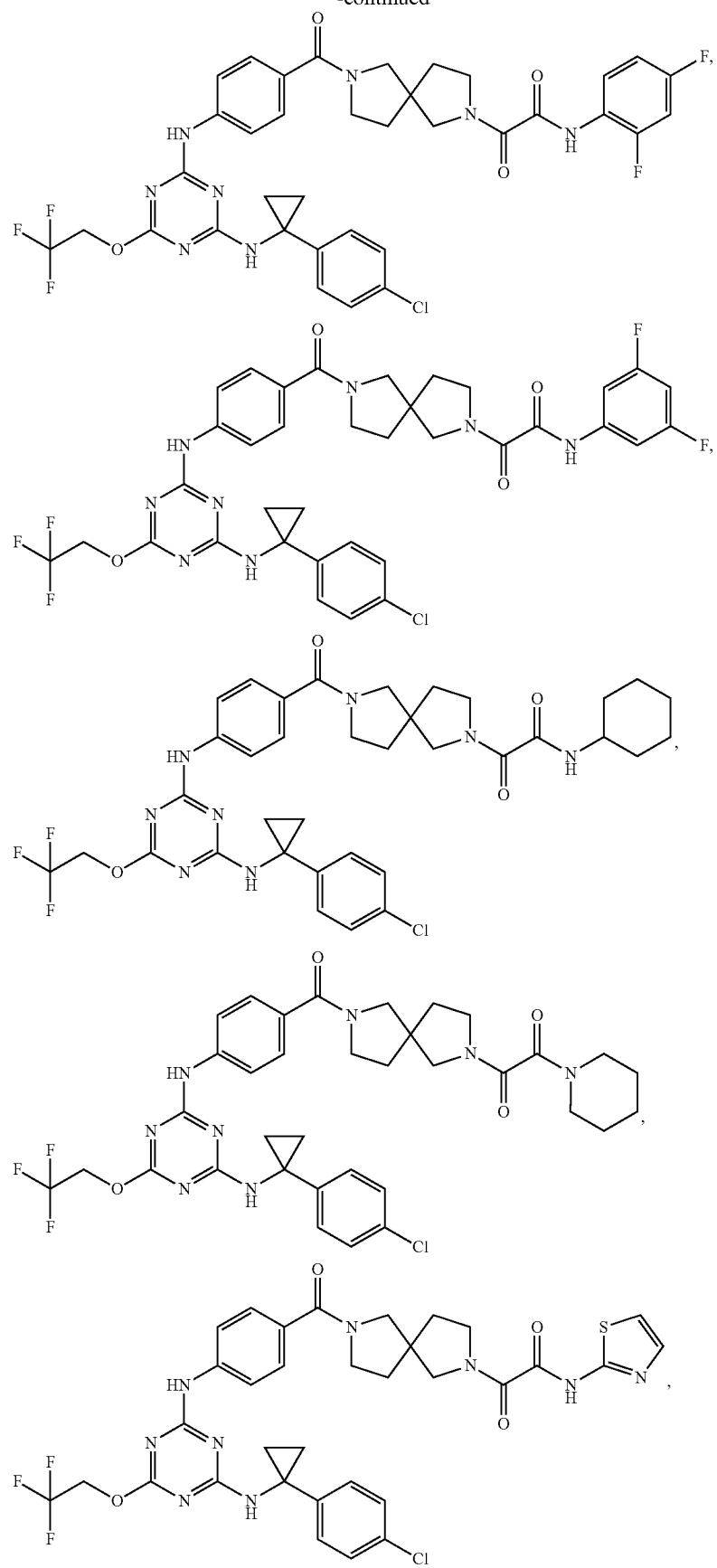

-continued
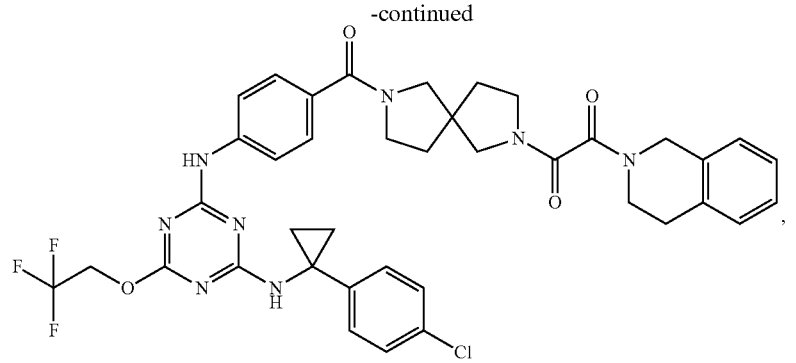
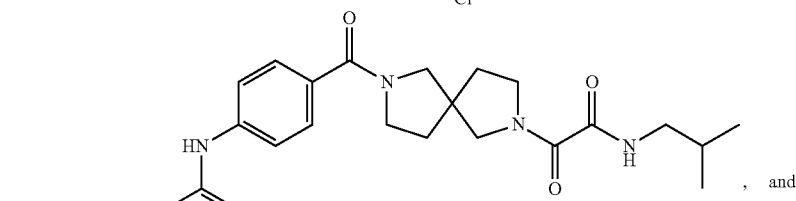, and
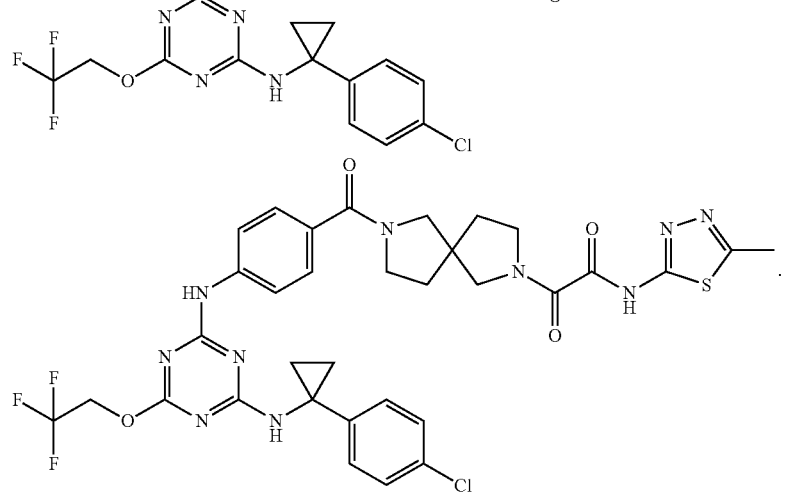.
14. A pharmaceutical composition comprising one or more compounds of claim 13, and a pharmaceutically acceptable carrier.
* * * * *